US007981691B2

(12) United States Patent (10) Patent No.: US 7,981,691 B2
Hoerner et al. (45) Date of Patent: Jul. 19, 2011

(54) TWO HELIX BINDERS

(75) Inventors: Joshua Kendall Hoerner, Madison, NJ (US); Rong Zhang, Niskayuna, NY (US); Faisal Ahmed Syud, Clifton Park, NY (US); Jack Mathew Webster, Colonie, NY (US)

(73) Assignee: General Electric Company, Niskayuna, NY (US)

( * ) Notice: Subject to any disclaimer, the term of this patent is extended or adjusted under 35 U.S.C. 154(b) by 272 days.

(21) Appl. No.: 12/337,933

(22) Filed: Dec. 18, 2008

(65) Prior Publication Data

US 2010/0041073 A1 Feb. 18, 2010

Related U.S. Application Data

(63) Continuation-in-part of application No. 11/608,590, filed on Dec. 8, 2006.

(51) Int. Cl.
*A61K 38/00* (2006.01)
*G01N 33/53* (2006.01)
*G01N 33/574* (2006.01)

(52) U.S. Cl. ........ 436/501; 530/323; 530/317; 435/7.23
(58) Field of Classification Search .................. None
See application file for complete search history.

(56) References Cited

U.S. PATENT DOCUMENTS

| 5,831,012 A | 11/1998 | Nilsson et al. |
| 6,013,763 A | 1/2000 | Braisted et al. |
| 2003/0219853 A1 | 11/2003 | Chou |
| 2008/0125347 A1 | 5/2008 | Grabstein et al. |

FOREIGN PATENT DOCUMENTS

| WO | 0063243 A1 | 10/2000 |
| WO | 2005003156 A1 | 1/2005 |

OTHER PUBLICATIONS

M.Wikman, A.C.Steffen, E.Gunneriusson, V.Tolmachev, G.P. Adams, J.Carlsson and S.Stahl; "Selection and characterization of HER2/neu-binding affibody ligands"; Protein Engineering, Design & Selection vol. 17 No. 5 ᵃ Oxford University Press 2004; all rights reserved; Protein Engineering, Design & Selection vol. 17 No. 5 pp. 455-462, 2004. Published online Jun. 18, 2004 doi:10.1093/protein/gzh053.
Anna Orlova, Fredrik Y. Nilsson, Maria Wikman, Charles Widstrom, Stefan Stahl, Jorgen Carlsson and Vladimir Tolmachev; "Comparative In Vivo Evaluation of Technetium and Iodine Labels on an Anti-HER2 Affibody for Single-Photon Imaging of HER2 Expression in Tumors"; The Journal of Nuclear Medicine • vol. 47 • No. 3 • Mar. 2006; pp. from 512-519.
Torun Engfeldt, Bjcrn Renberg, Harry Brumer, Per_Ke Nygren, and Amelie Eriksson Karlstrcm; "Chemical Synthesis of Triple-Labelled Three-Helix Bundle Binding Proteins for Specific Fluorescent Detection of Unlabelled Protein"; DOI: 10.1002/cbic.200400388; ChemBioChem 2005, 6, 1043-1050.

E.Gunneriusson, K.Nord, M.Uhltn and P.A.Nygren; "Affinity maturation of a Taq DNA polymerase specific affibody by helix shuffling"; Protein Engineering vol. 12 No. 10 pp. 873-878, 1999.
Maria N Nedwidek and Michael H Hecht; "Minimized protein structures: A little goes a long way"; Departments of 'Molecular Biology and Chemistry. Princeton University, Princeton, NI08544; Proc Nall. Acad. Sci. USA. vol. 94, pp. 10010-10011, Sep. 1997.
Thomas Hey, Erik Fiedler, Rainer Rudolph and Markus Fiedler; "Artificial, non-antibody binding proteins for pharmaceutical and industrial applications"; Trends in Biotechnology vol. 23 No. 10 Oct. 2005; 514-522pages.
Elisabet Wahlberg, Christofer Lendel, Magnus Helgstrand, Peter Allard, Vildan Dincbas-Renqvist, Anders Hedqvist, Helena Berglund, Per-Ake Nygren and Torleif Hard; "An affibody in complex with a target protein: Structure and coupled folding"; Department of Biotechnology, Royal Institute of Technology, S-106 91 Stockholm, Sweden; Edited by Adriaan Bax, National Institutes of Health, Bethesda, MD, and approved Dec. 27, 2002 (received for review Oct. 9, 2002); 3185-3190pages.
Melissa A. Starovasn1k, Andrew C. Braisted and James A. Wells; "Structural mimicry of a native protein by a minimized binding domain"; Department of Protein Engineering, Genentech, Inc., I DNA Way, South San Francisco, CA 94080; vol. 94, pp. 10080-10085, Sep. 1997.
Vladimir Tolmachev, Fredrik Y. Nilsson, Charles Widstrom, Karl Andersson , Daniel Rosik , Lars Gedda ,Anders Wennborg, and Anna Orlova; "In-Benzyl-DTPA-ZHER2:342, An Affibody-Based Conjugate for In Vivo Imaging of HER2 Expression in Malignant Tumors"; The Journal of Nuclear Medicine • vol. 47 • No. 5—May 2006.J Nuel Med 2006; 47:846-853.
Andrew C. Bralsted and James A. Wells; "Minimizing a binding domain from protein A"; Department of Protein Engineering, Genentech, Inc., 460 Poinl San Bruno Boulevard, South San Francisco, CA 94080; vol. 93, pp. 5688-5692, Jun. 1996.
Helen E. Blackwell and Robert H. Grubbs; "Highly Efficient Synthesis of Covalently Cross-Linked Peptide Helices by Ring-Closing Metathesis"; Angew. Chem. Int. Ed. 1998, 37, No. 23; 3281-3284pages.
Myung Kyu Lee, Hee Kyung Kim,Tae Young Lee, Kyung-Soo Hahm and Kil Lyong Kim; "Structure-activity relationships of anti-HIV-1 peptides with disulfide linkage between D- and L-cysteine at positions i and i+3, respectively, derived from HIV-1 gp41 C-peptide"; Experimental and Molecular Medicine, vol. 38, No. 1, Feb. 18-26, 2006.
Christopher Bystroff and Shekhar Garde; "Helix Propensities of Short Peptides: Molecular Dynamics Versus Bioinformatics"; Received Oct. 12, 2001; Accepted Jul. 24, 2002; Proteins: Structure, Function, and Genetics 50:552-562 (2003).

(Continued)

*Primary Examiner* — Manjunath N Rao
*Assistant Examiner* — Kagnew H Gebreyesus
(74) *Attorney, Agent, or Firm* — Jenifer E. Haeckl

(57) ABSTRACT

An isolated polypeptide, Z domain, derived from B domain of *Staphylococcal* protein A, comprising a pair of anti-parallel alpha helices that are capable of binding a target, is provided herein. Introduction of a covalent bridge between two modified amino acids in the polypeptide is provided here. Also provided are methods of using the two-helix binders.

7 Claims, 20 Drawing Sheets

OTHER PUBLICATIONS

J. Christopher Phelan, Nicholas J. Skelton, Andrew C. Braisted and Robert S. McDowell; "A General Method for Constraining Short Peptides to an R-Helical Conformation"; ReceiVed Apr. 8, 1996. ReVised Manuscript ReceiVed Sep. 16, 1996X; S0002-7863(96)01165-1 CCC: $14.00.

Christian E. Schafmeister, Julia Po, and Gregory L. Verdine; "An All-Hydrocarbon Cross-Linking System for Enhancing the Helicity and Metabolic Stability of Peptides"; Published on Web Jun. 6, 2000. 10.1021/ja000563a CCC: $19.00.J. Am. Chem. Soc. 2000, 122, 5891-5892pages.

Andrea G. Cochran, Ricky T. Tong, Melissa A. Starovasnik, Eleanor J. Park, Robert S. McDowell, J. E. Theaker and Nicholas J. Skelton; "A Minimal Peptide Scaffold for â-Turn Display: Optimizing a Strand Position in Disulfide-Cyclized â-Hairpins"; ReceiVed Sep. 13, 2000; Published on Web Dec. 28, 2000; J. Am. Chem. Soc. 2001, 123, 625-632pages.

Joachim Feldwisch, Anna Orlova, Anders Wennborg, Fredrik Nilsson, Rikard Pehrson and Vladimir Tolmachev; "Targeting and Molecular Imaging of Cancer Using anti-HER2 Affibody Molecules"; Affibody AB, P.O. Box 20137, SE-161 02 Bromma, Sweden, www.affibody.com; 1page.

Pooja Arora, Terrence G. Oas and Jeffrey K. Myers; "Fast and faster: A designed variant of the B-domain of protein A folds in 3sec"; Protein Science (2004), 13:847-853. Published by Cold Spring Harbor Laboratory Press. Copyright © 2004 The Protein Society.

Loren D. Walensky, Andrew L. Kung, Iris Escher, Thomas J. Malia, Scott Barbuto, Renee D. Wright, Gerhard Wagner, Gregory L. Verdine, Stanley J. Korsmeyer; "Activation of Apoptosis in Vivo by a Hydrocarbon-Stapled BH3 Helix"; Sep. 3, 2004 vol. 305 Science www.sciencemag.org Downloaded from www.sciencemag.org on Feb. 16, 2007; 1466-1470pages.

```
                        d b c
Anti-Her2    VENKCNKEMRNAYWEIALLPNLNNQQKRAFIRSLYDDPC
```

FIG. 7B

VENKC²NKE¹MRNAYWE¹IALLPNLNNQQKRAFIRSLYDDPC²

Where,

E¹ is O-allyl glutamic acid [(S)-5-(allyloxy)-2-amino-5-oxopentanoic acid
RCM is Ring Closure Metathesis
C² - Extended cysteim

TWO HELIX BINDERS

CROSS REFERENCE TO RELATED APPLICATIONS

Sequence Listing

The application contains a Sequence Listing which has been submitted via EFS-Web and is hereby incorporated by reference in its entirety. The ASCII copy, created on Oct. 12, 2009, is named 215536-3.txt, and is 34,131 bytes in size.

This application is a continuation-in-part of U.S. patent application Ser. No. 11/608,590, entitled "Two helix binders", filed Dec. 8, 2006, which is herein incorporated by reference.

FIELD

The field of invention relates to polypeptides that form multiple helices and are capable of binding to a target.

BRIEF DESCRIPTION

A polypeptide contains 2-alpha helices and a binding surface that isolated from Z-domain of *Staphylococcal* protein A. The present invention provides a polypeptide containing two helices that is stabilized with a covalent bridge introduced between two amino acids or its analogs. It also increases the affinity of the peptide to bind various targets.

In some embodiments, the sequence consists of SEQ ID No. 12 or a four-residue N-terminal truncated variant of SEQ ID NO. 12; and conservative variants thereof is provided wherein, $E^1$ is selected from an O-allyl glutamic acid or its analog thereof. In some embodiments, a covalent bridge is present between two $E^1$ residues that stabilizes the peptide and increases its binding affinity.

In other embodiments, an isolated polypeptide of SEQ ID NO. 30 or a four-residue N-terminal truncated variant of SEQ ID NO. 30 and conservative variants thereof is provided wherein $E^1$ is selected from an o-allyl glutamic acid or its analog thereof. In some embodiments, a covalent bridge formed between two $E^1$ residues that stabilizes the peptide and increases its binding affinity. In some embodiments, X is an alpha amino isobutyric acid or its analog that is introduced which increases its binding affinity.

In some embodiments, an isolated polypeptide of SEQ ID NO. 31 or a four-residue N-terminal truncated variant of SEQ ID NO. 31 and conservative variants thereof is provided wherein, $E^1$ is selected from an O-allyl glutamic acid or its analog thereof. In other embodiments, a covalent bridge formed between two $E^1$ residues that stabilizes the peptide and increases its binding affinity. In one embodiment, X is alpha amino isobutyric acid or its analog that is introduced which increases binding affinity. In other embodiment, the amino acid substitutions made in the polypeptide are A12R, I16A, L19D, F30K and L34I that also increase binding affinity.

In other embodiments, an isolated polypeptide of SEQ ID NO. 32 or a four-residue N-terminal truncated variant of SEQ ID NO. 32 and conservative variants thereof is provided wherein; $E^1$ is selected from an O-allyl glutamic acid or its analog thereof. In some embodiments, a covalent bridge formed between two $E^1$ residues that stabilizes the peptide and increases its binding affinity. In other embodiments, X is alpha amino isobutyric acid or its analog that is introduced which increases binding affinity. Embodiments also describe, the incorporation of C2, which is extended cysteine and a disulfide bond, connects the C2 residues that stabilizes the peptide and increases the binding affinity. Embodiments further describes, the amino acid substitutions made in the polypeptide are A12R, I16A, L19D, F30K and L34I that also increase binding affinity.

FIGURES

These and other features, aspects, and advantages of the present invention will become better understood when the following detailed description is read with reference to the accompanying figures.

FIG. 1 depicts the relative binding analysis of crude peptide with and without engineered cysteines. Approximately 5 μg/ml of crude product from each peptide synthesis was analyzed for binding to Her2 using surface plasmon resonance (Biacore).

FIG. 2 depicts RP-HPLC analysis of purified anti-Her2 two helix peptide (SEQ. ID. NO.:8) with Acm-protected cysteines compared to the Iodine deprotected-oxidized anti-Her2 two-alpha helix peptide with a disulfide bond. Two peptides compared using the same RP-HPLC conditions. Control Acm-protected anti-Her2 two-alpha-helix peptide has a retention time of 19.49 minutes. The iodine treated peptide has a shift in retention time to 18.98 minutes. This change is a reflection of the loss of two Acm-protecting groups and formation of an intramolecular disulfide bond. Fractions corresponding to these two peaks were collected for analysis by mass spectrometry, and confirmed to be the claimed products.

FIG. 3 depicts ESI-MS analysis of the control peptide: Acm-protected cysteines. Collected fractions corresponding to the control Acm-protected peptide (shown in FIG. 4 with a retention time of 19.498) were analyzed by ESI-MS. The formula weight is as predicted for the desired peptide with two Acetamidomethyl groups protecting the cysteine side chain. Peptide+2(Acm) [4698.4+2(71)]=4840.4 daltons.

FIG. 4 depicts ESI-MS analysis of the anti-Her2 two helix peptide. Collected fractions corresponding to the $I_2$ deprotected/oxidized peptide shown in FIG. 4 with a retention time of 18.98. The formula weight is as predicted for the desired peptide with one disulfide bridge. Peptide+disulfide bond [4698.4−2(H)]=4696.4 daltons.

FIG. 5 shows the binding kinetics analysis of anti-Her2 two helix peptide (SEQ. ID. NO.:8), in which binding was measured with a range of concentrations of each peptide between 0-40 nM. The resulting curves were fit using BiaEval software to determine an estimated $K_D$. Curve fitting was not practical for the control peptide, as binding was minimal. Response difference on the X-axis refers to the difference between a Her2-immobilized flow-cell and a control flow-cell.

FIG. 6 shows binding kinetics analysis of anti-IgG two helix peptide (SEQ. ID. NO.7), in which binding was measured with a range of concentrations of each peptide between 0-1 μM. An anti-IgG two alpha-helix peptide was made in the same manner as the anti-Her2 peptide. The resulting curves were fit using BiaEval software to determine an estimated $K_D$. Curve fitting was not practical for the control peptide, as binding was minimal. Response difference on the X-axis refers to the difference between a Her2-immobilized flow-cell and a control flow-cell.

FIG. 7A depicts three potential arrangements of engineered cysteines and the effect on binding to target. Panel a shows the predicted structure of the stabilized two-alpha helix peptide backbone. An example of two potential alternative sites for engineering cysteines is shown with asterisks (*). Panel b shows an arbitrary orientation of the binding residues on the alpha helices. While Panels c and d show examples of how the orientation of the binding residues may change with respect to each other with alternative sites for engineered cysteine residues. These positional changes for a stabilizing disulfide bond will alter the affinity of the peptide for its binding partner, allowing affinity modulation and optimization.

FIG. 7B shows the sequence (SEQ ID NO: 8) of the anti Her2 two-alpha helix peptide, showing three potential sites for disulfide bond engineering described in FIG. 7, Panel A (SEQ. ID. NO.:8, SEQ. ID. NO.:9 and SEQ. ID. NO.:10).

Figure 9:
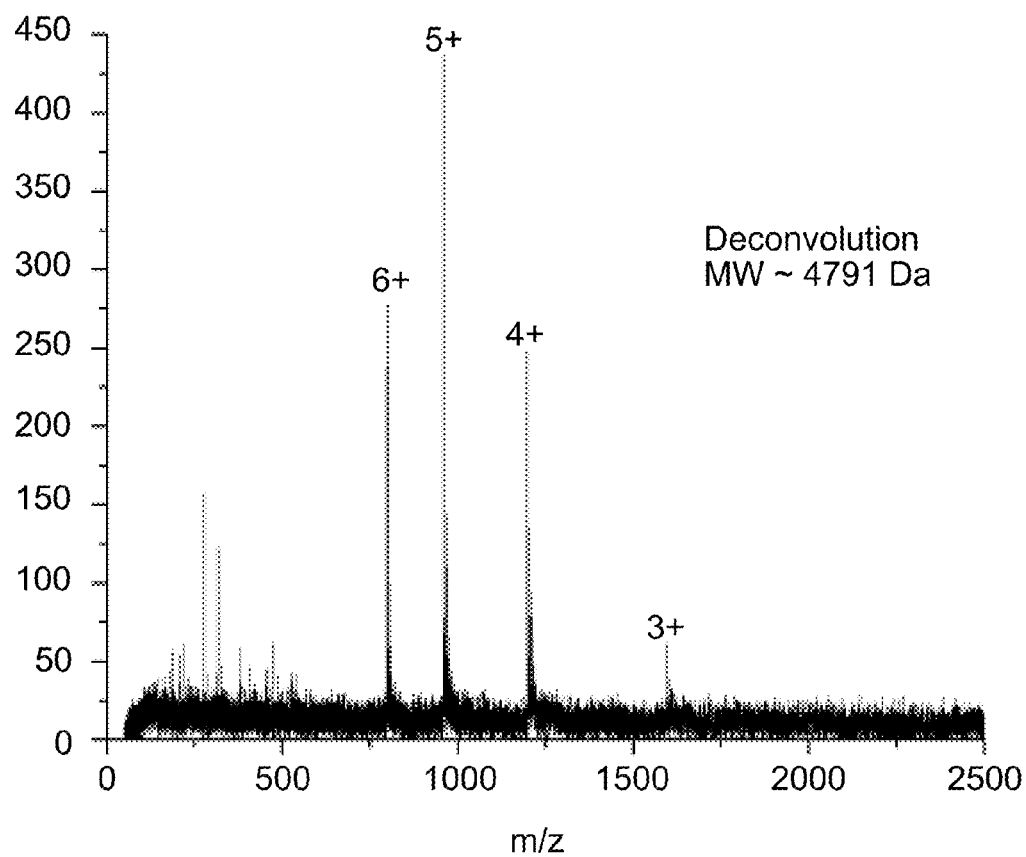

FIG. 9 depicts ESI-MS analysis of the peptide with a covalent bridge between two $E^1$ residues (SEQ. ID. NO. 12).

Figure 10A:
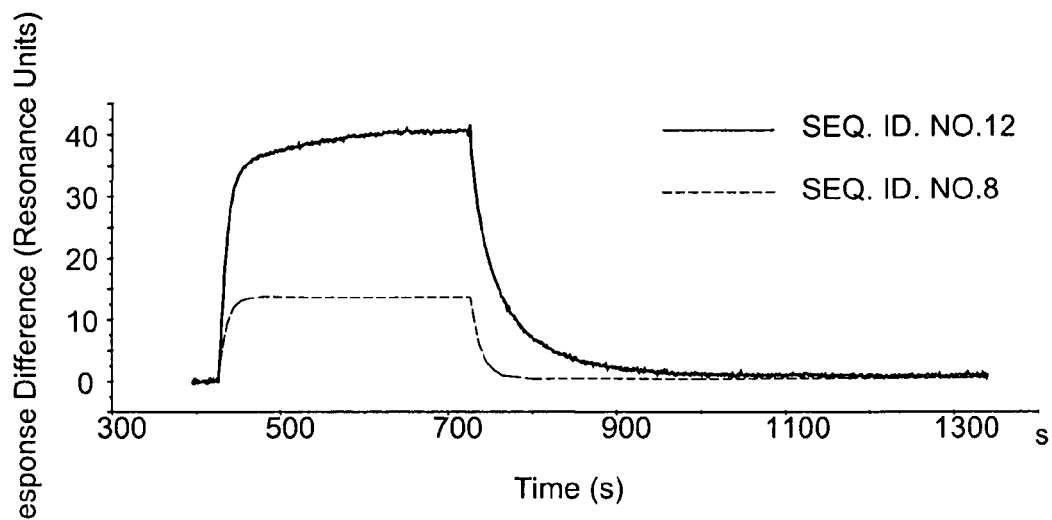
Figure 10B:
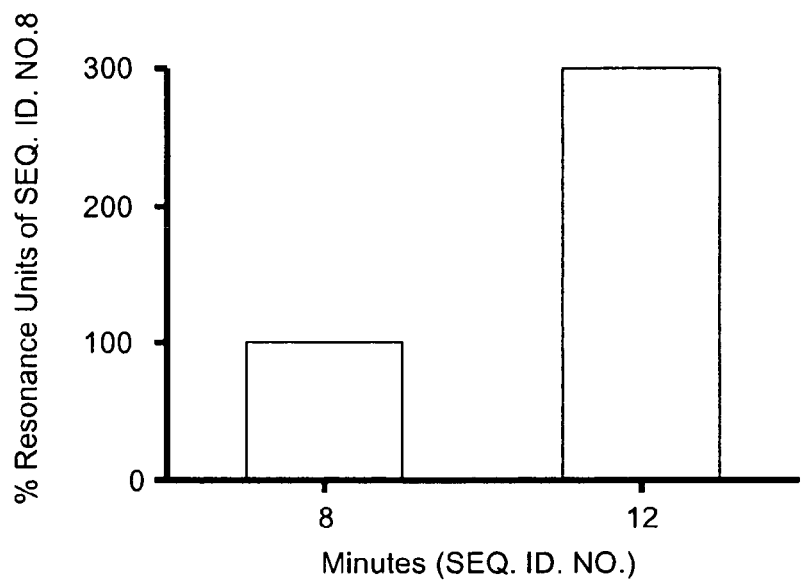

FIG. 10 depicts the relative binding analysis of peptide having covalent bridge and the peptide without covalent bridge. Approximately 5 μg/ml of product from each peptide synthesis was analyzed for binding to Her2 using surface plasmon resonance (Biacore). FIG. 10 (A) shows binding curves and FIG. 10 (B) shows detectable binding by bar graph for SEQ. ID. NO. 8 and SEQ. ID. NO. 12.

Figure 11:
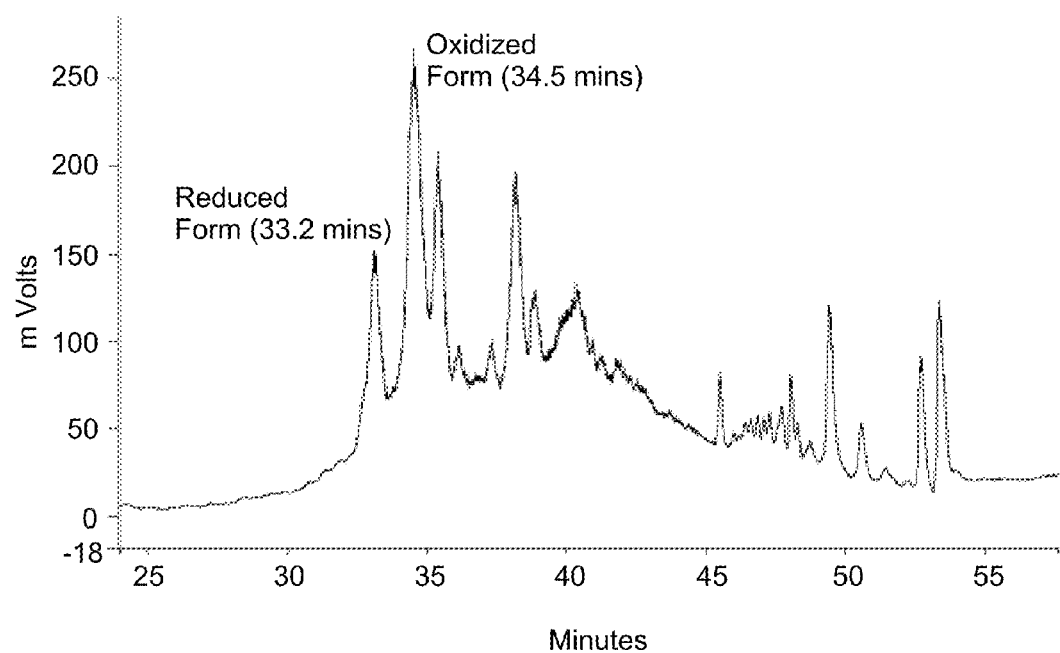

FIG. 11 depicts RP-HPLC analysis of Iodine deprotection-oxidation reaction of the anti-Her2 two helix peptide (SEQ. ID NO. 21). The oxidized form and the reduced form of the peptide showed a retention time of 33.2 and 34.5 mins, respectively. Fractions corresponding to these two peaks were collected for analysis by mass spectrometry, and confirmed to be the claimed products.

Figure 12A:
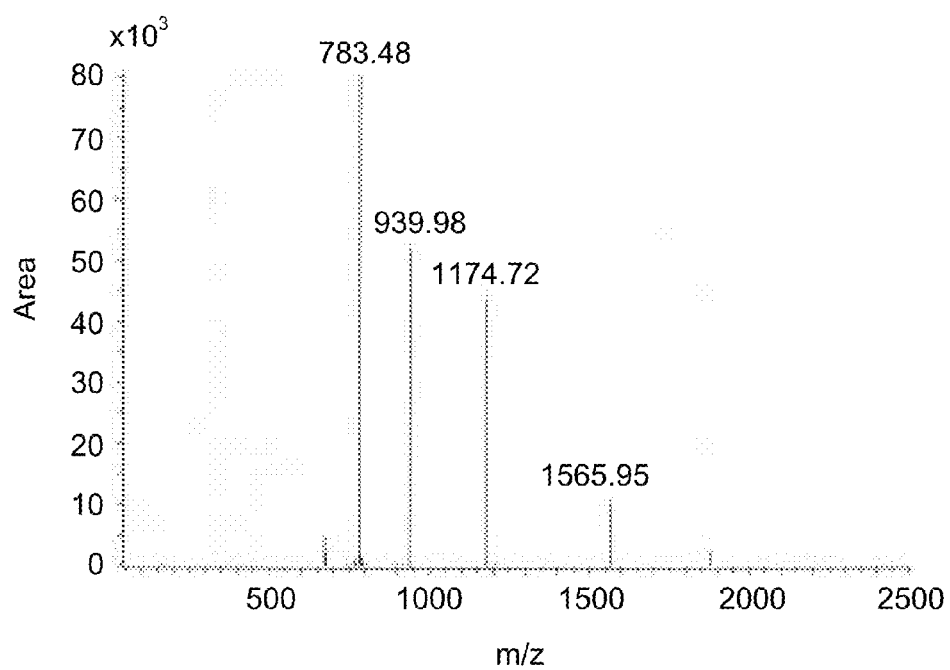
Figure 12B:
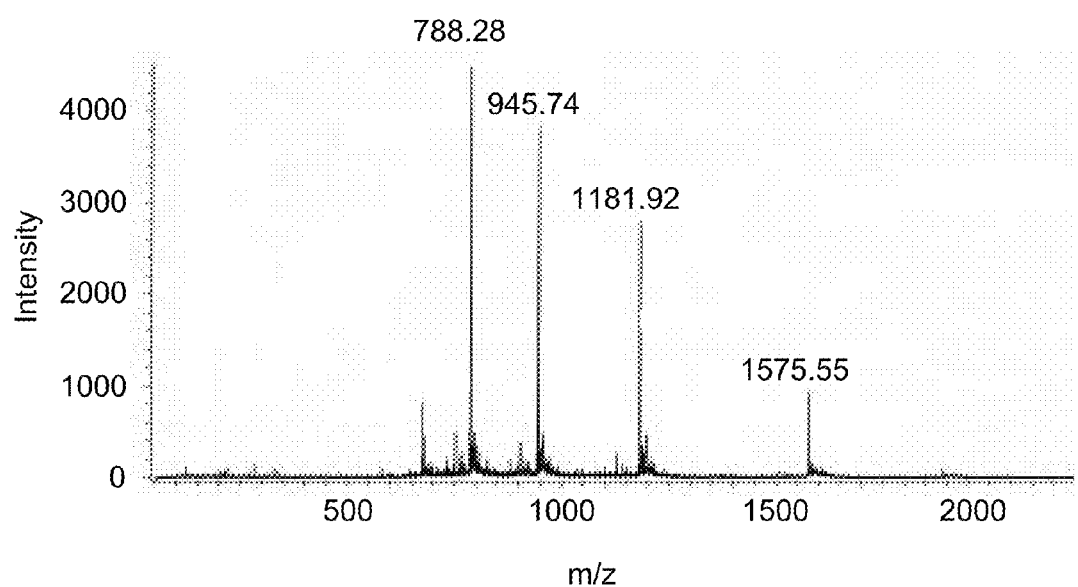

FIG. 12 depicts ESI-MS analysis of (A) SEQ. ID. NO. 8 and (B) the oxidized peptide with disulfide bond (SEQ. ID. NO. 21), which corresponds to the fraction collected at 33.2 mins in FIG. 11.

Figure 13A:
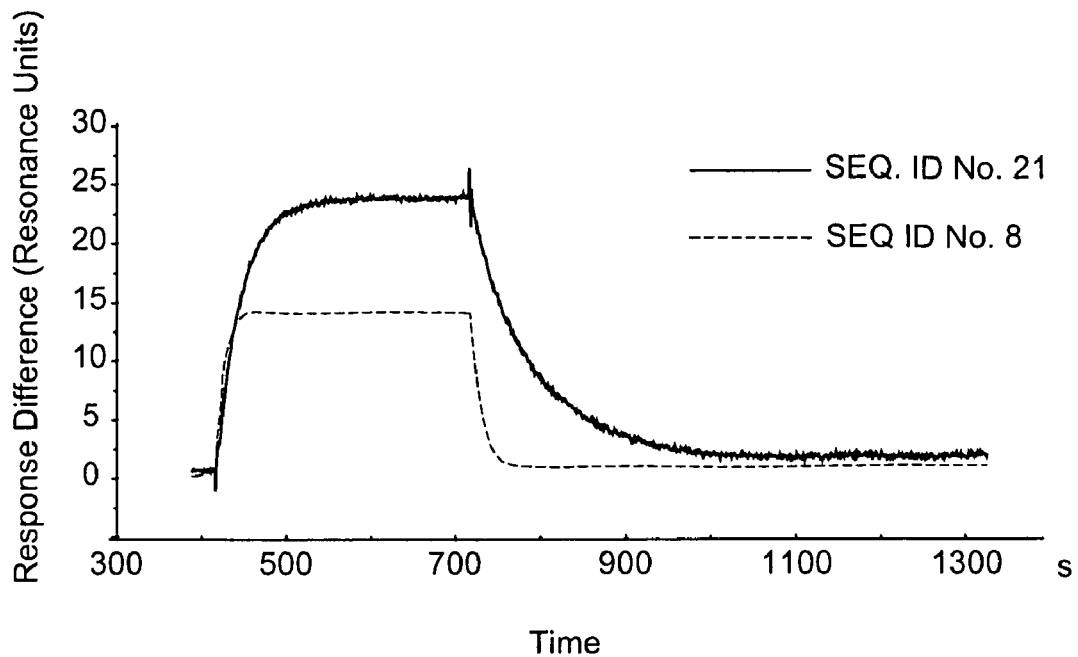
Figure 13B:
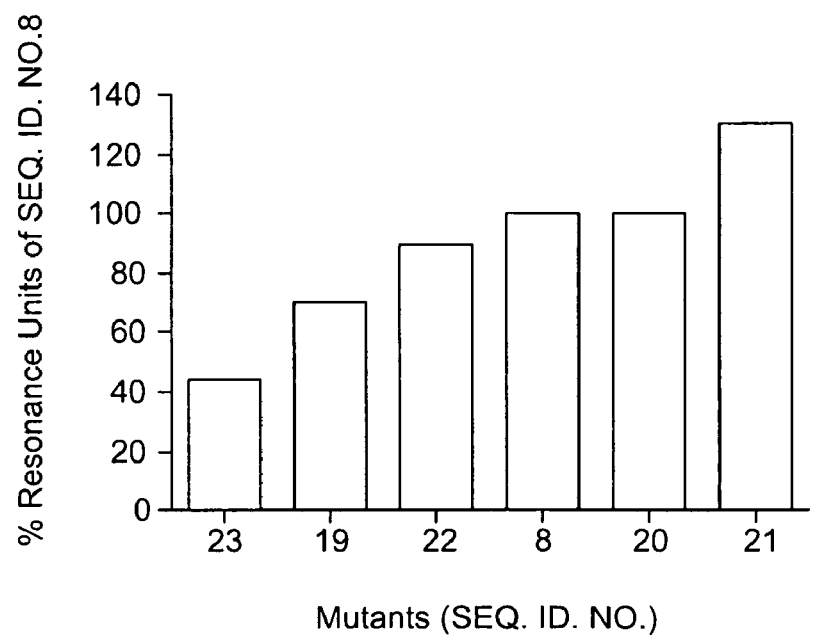

FIG. 13 depicts the relative binding analysis of peptide with different cysteine variants. Approximately 5 μg/ml of product from each peptide synthesis was analyzed for binding to Her2 using surface plasmon resonance (Biacore). Panel (A) shows binding curves for SEQ. ID. NO. 8 and SEQ. ID. NO. 21. Panel (B) shows detectable binding for the two-alpha-helix peptides with different combination of disulfide bridges for SEQ. ID. No's: 23, 19, 22, 8, 20 and 21.

Figure 14A:
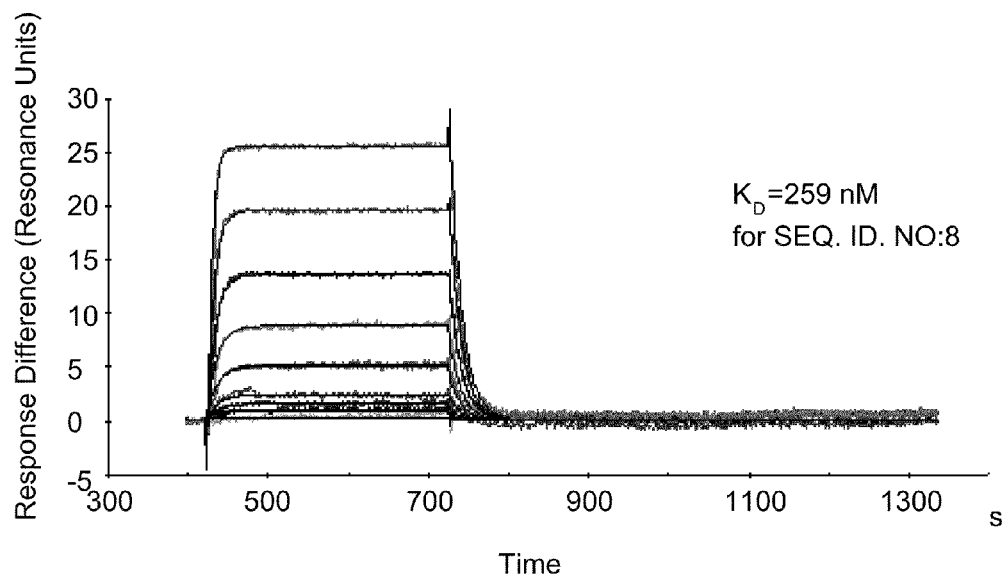
Figure 14B:
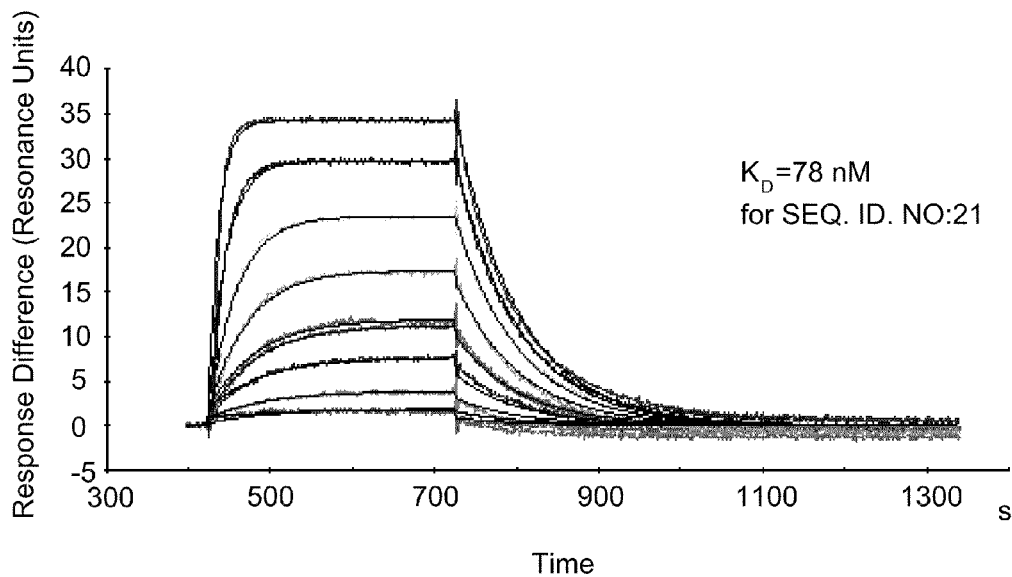

FIG. 14 shows binding kinetic analysis of anti-Her2 two helix peptide (A) SEQ. ID. NO. 8 and (B) SEQ. ID. NO. 21 in which bindings were measured with a range of concentrations of each peptide between 0-100 nM. The resulting curves were fit using BiaEval software to determine an estimated $K_D$. Response difference on the X-axis refers to the difference between a Her2-immobilized flow-cell and a control flow-cell.

Figure 15A:
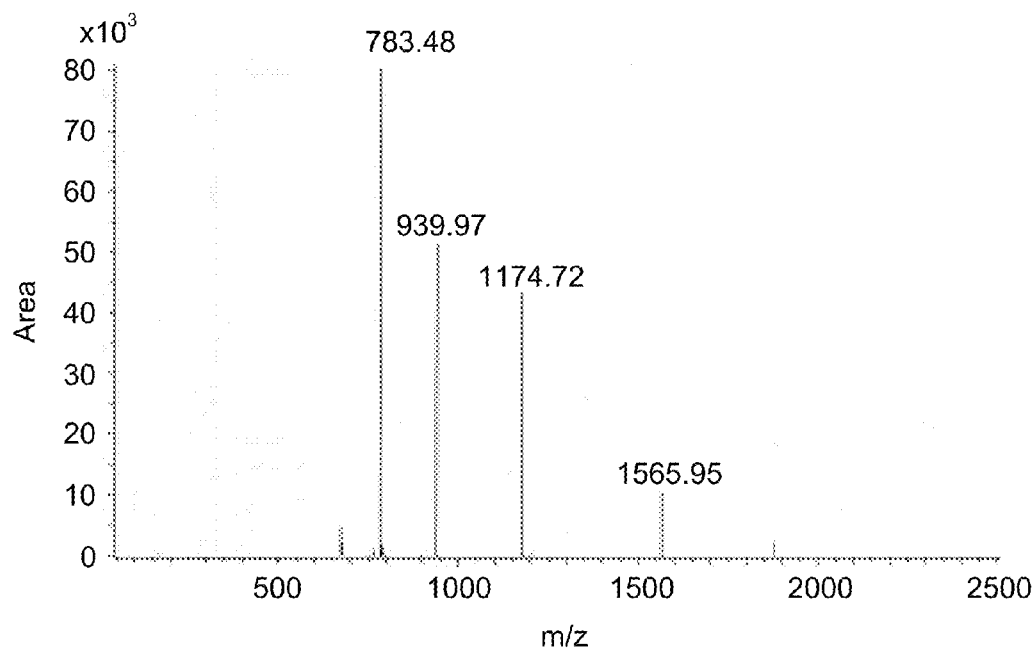
Figure 15B:
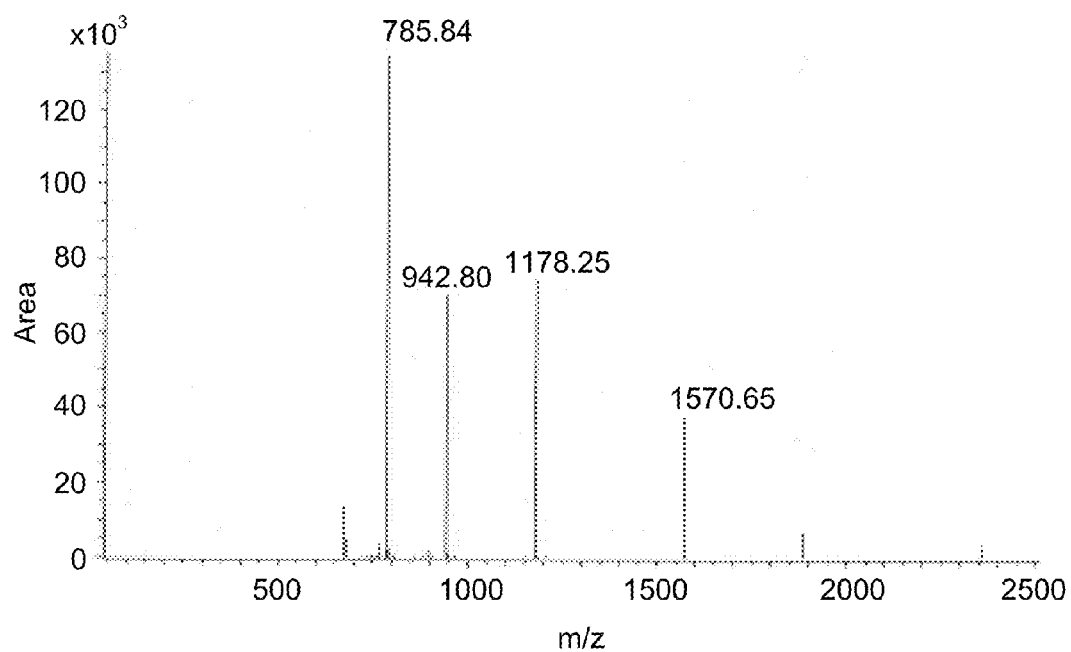

FIG. 15 depicts ESI-MS analysis of (A) a control peptide (SEQ. ID. NO. 8) and for (B) the peptide with Ala29Aib (SEQ. ID. NO. 27). The molecular weight is conformed by ESI-MS.

Figure 16A:
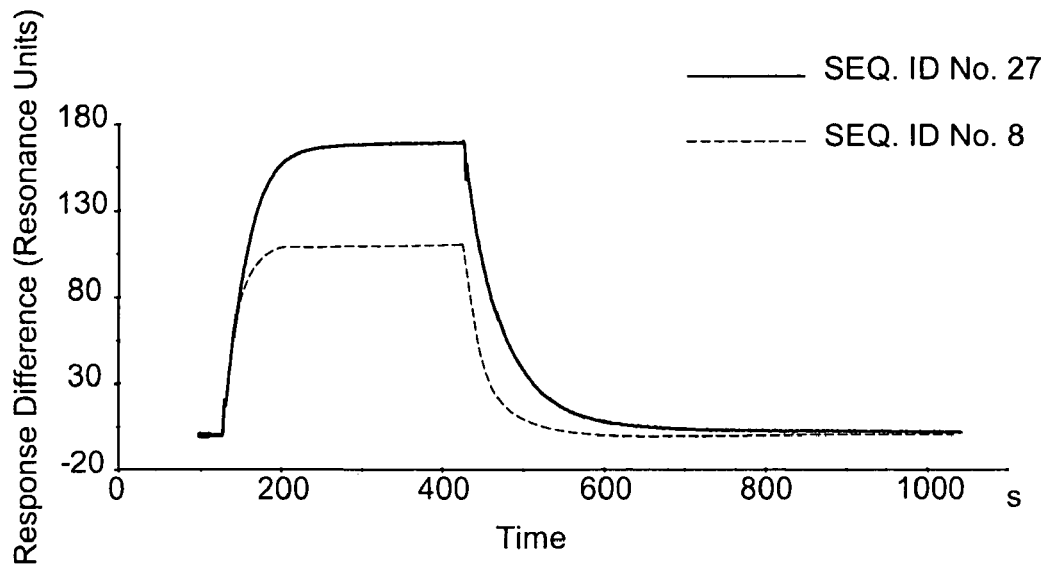
Figure 16B:
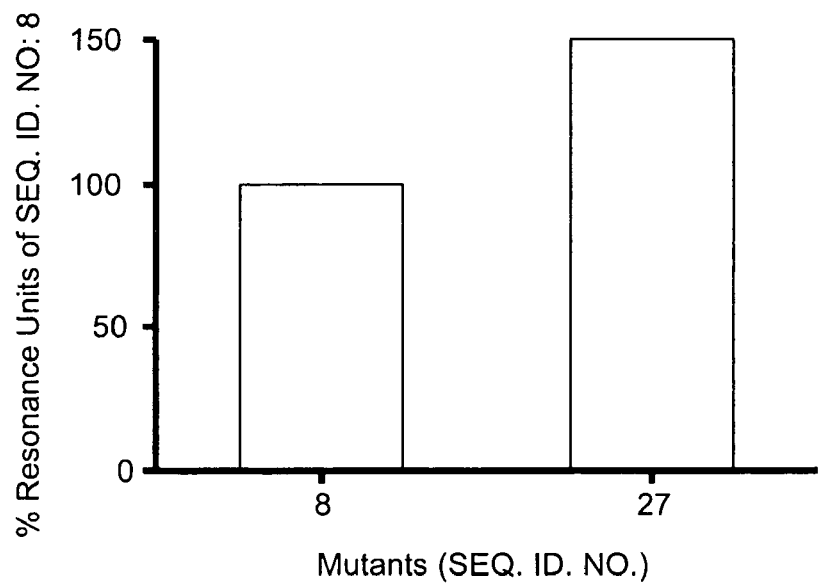

FIG. 16 depicts the relative binding analysis of peptide with and without Aib substituted mutants. Approximately 5 μg/ml of product from each peptide synthesis was analyzed for binding to Her2 using surface plasmon resonance (Biacore). FIG. 16 (A) shows binding curves for SEQ. ID. NO. 8 and SEQ. ID. NO. 27 and FIG. 16 (B) show detectable binding by bar graph for SEQ. ID. NO. 8 and SEQ. ID. NO. 27.

Figure 17A:
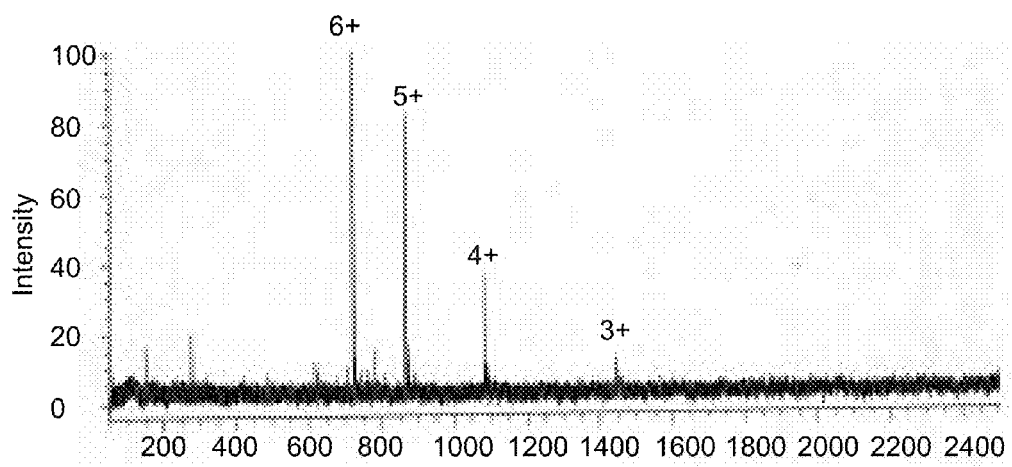
Figure 17B:
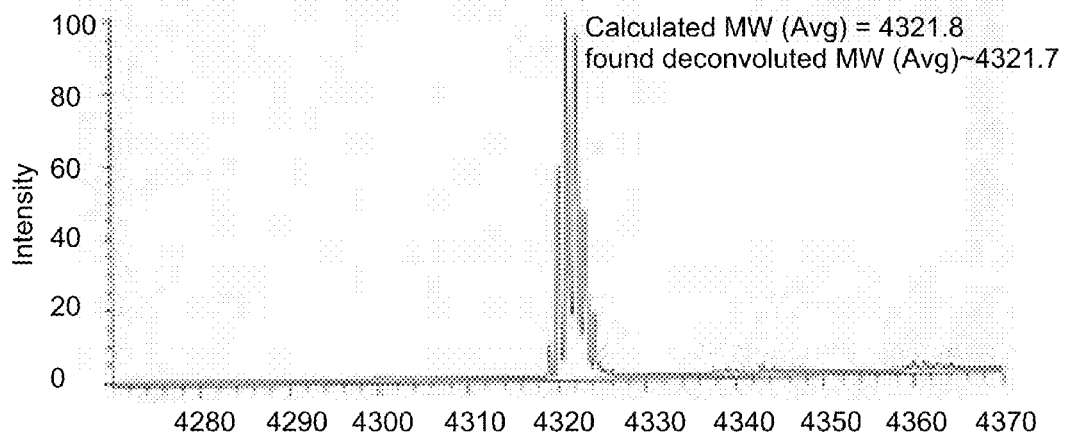

FIG. 17(A) shows the ESI-MS analysis of the peptide (SEQ. ID. NO. 29) with five different natural amino acid mutations and FIG. 17 (B) shows the deconvoluted molecular weight (MW) of the peptide (SEQ. ID. NO. 29).

Figure 18A:
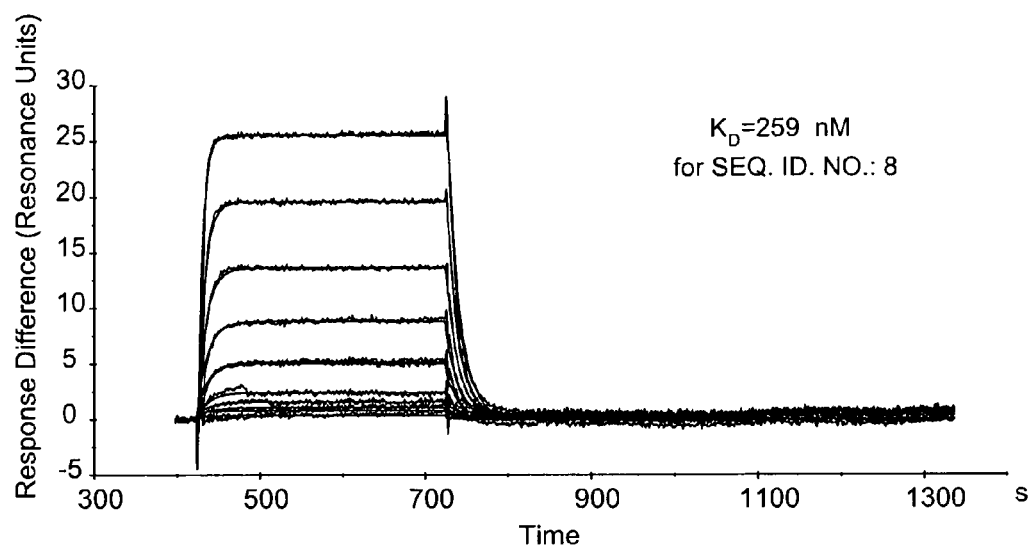
Figure 18B:
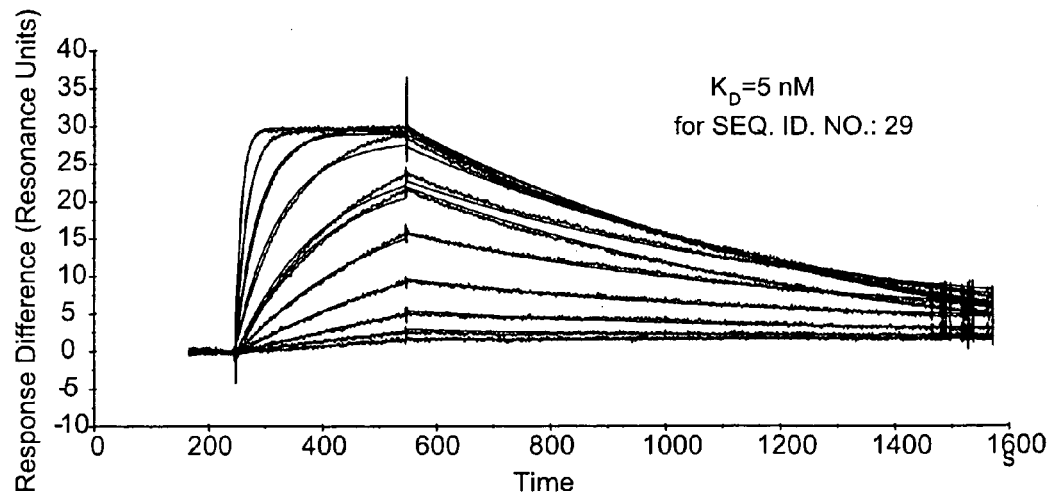

FIG. 18 shows binding kinetic analysis of anti-Her2 two helix peptide (A) SEQ. ID. NO. 8 and (B) SEQ. ID. NO. 29 in which bindings were measured with a range of concentrations of each peptide between 0-100 nM. The resulting curves were fit using BiaEval software to determine an estimated $K_D$. Response difference on the X-axis refers to the difference between a Her2-immobilized flow-cell and a control flow-cell.

DETAILED DESCRIPTION

The following detailed description is exemplary and not intended to limit the invention of the application and uses of the invention. Furthermore, there is no intention to be limited by any theory presented in the preceding background of the invention of the following detailed description. To more clearly and concisely describe and point out the subject matter of the claimed invention, the following definitions are provided for specific terms that are used in the following description and the claims appended hereto.

Unless otherwise indicated, the word "a" refers to one or more than one of the word modified by the article "a."

The term "amino acid" refers to both naturally occurring and synthetic amino acids. It also includes amino acid analogs and amino acid mimetics that function in a manner similar to the naturally occurring amino acids. Naturally occurring amino acids are the ones encoded by genetic code. The naturally occurring amino acids may further get modified, such as hydroxyproline, γ-carboxyglutamate, O-phosphoserine, phosphothreonine, or phosphotyrosine. Categories of amino acids herein defined are not mutually exclusive. Thus, amino acids having side chains exhibiting two or more physical-chemical properties can be included in multiple categories. For example, amino acid side chains having aromatic moieties that are further substituted with polar substituents, such as Tyr (Y), may exhibit both aromatic hydrophobic properties and polar or hydrophilic properties, and can therefore be included in both the aromatic and polar categories. The appropriate categorization of any amino acid will be apparent to those of skill in the art, in light of the detailed disclosure provided herein.

"Acidic Amino Acid" refers to a hydrophilic amino acid having a side chain pKa value of less than 7. Acidic amino acids typically have negatively charged side chains at physiological pH due to loss of a hydrogen ion. Genetically encoded acidic amino acids include Glu (E) or Asp (D).

"Aliphatic Amino Acid" refers to a hydrophobic amino acid having an aliphatic hydrocarbon side chain. Genetically encoded aliphatic amino acids include Ala (A), Val (V), Leu (L), and Ile (I).

"Amino acid analogs" refer to compounds that contain a modification either at the amino acid side chain or at the amino acid peptide backbone. It may include an amino acid having a peptide backbone, which is similar to that of a naturally occurring amino acid (i.e., a carbon that is bound to a hydrogen, a carboxyl group, an amino group) and a non-conventional functional group attached to the alpha carbon (R group) (e.g., homoserine, norleucine, methionine sulfoxide, or methionine methyl sulfonium).

"Aromatic Amino Acid" refers to a hydrophobic amino acid with a side chain having at least one aromatic or heteroaromatic ring. The aromatic or heteroaromatic ring may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR and the like where each R is independently $(C_1-C_6)$alkyl, substituted $(C_1-C_6)$alkyl, $(C_1-C_6)$ alkenyl, substituted $(C_1-C_6)$alkenyl, $(C_1-C_6)$alkynyl, substituted $(C_1-C_6)$alkynyl, $(C_5-C_{20})$aryl, substituted $(C_5-C_{20})$aryl, $(C_6-C_{26})$alkaryl, substituted $(C_6-C_{26})$alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe (F), Tyr (Y), and Trp (W).

"Amino isobutyric acid analog" refers to compounds that have same chemical backbone as that of isobutyric acid. Such analogs have modified R group, but restoring the same chemical backbone of isobutyric acid. Some amino isobutyric acid analogs are known to promote the helicity and rigidity of the 2-helix construct. Generally, these analogs function in a similar manner to those of parent amino acids.

2-Amino isobutyric acid (Aib)

"O-allyl glutamic acid analog" refers to compounds that have the same chemical backbone as a naturally occurring glutamic acid (i.e., a carbon that is bound to a hydrogen, a carboxyl group, an amino group) containing an 'allyl' group attached to its carboxylic oxygen. Such analogs may have modified R groups or modified peptide backbones, but retain the same basic chemical structure as a naturally occurring amino acid. They function in a manner similar to the naturally occurring amino acids. O-allyl glutamic acid refers (S)-5-(allyloxy)-2-amino-5-oxopentanoic acid. In some embodiments, O-allyl aspartic acid or long chain olefin substituted amino acids are also mentioned. O-allyl aspartic acid refers (S)-4-(allyloxy)-2-amino-4-oxobutanoic acid and C-allyl refers (2S)-Fmoc-2-amino-8-nonenoic acid. Glutamic acid or aspartic acid with O-allyl is selected as for olefin residues due to their ready availability and easy derivatization as allyl ethers. Some examples of allyl-substituted amino acids are shown in structures $E^1$, $D^1$ and C-allyl.

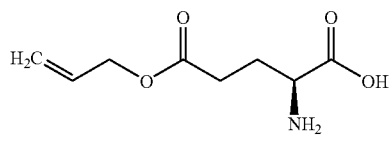

$E^1$ = (S)-5-(allyloxy)-2-amino-5-oxopentanoic acid

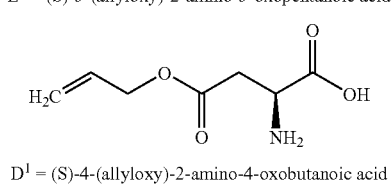

$D^1$ = (S)-4-(allyloxy)-2-amino-4-oxobutanoic acid

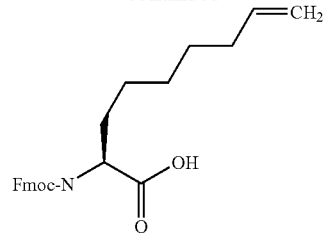

C-allyl = (2S)-Fmoc-2-amino-8-nonenoic acid

"Basic Amino Acid" refers to a hydrophilic amino acid having a side chain pKa value of greater than 7. Basic amino acids typically have positively charged side chains at physiological pH due to association with hydronium ion. Genetically encoded basic amino acids include His (H), Arg (R), and Lys (K).

As used herein, the term "binding" refers to the ability of a two helix binder to preferentially bind to target with an affinity that is at least two-fold greater than its affinity for binding to a non-specific target (e.g., BSA or casein) other than the predetermined target or a closely-related target. The two helix binders provided herein bind their respective targets with an affinity with a dissociation constant $(K_D)$ value less than about $5 \times 10^{-5}$ M, more preferably less than about $2 \times 10^{-7}$ M, and most preferably less than about $1 \times 10^{-8}$ M. Similarly, "specific binding" refers to the property of a binder to bind to a predetermined antigen with an affinity with a $K_D$ value less than about $2 \times 10^7$ M.

The terms "binding interface residue" and "binding interface residues" refer to those residues of the two helix binder polypeptide involved in target binding, which are exemplified in the representative 39-residue polypeptide shown in Table 1.

The term "binding surface" refers to that surface or region of the two helix binder polypeptide involved in target binding. A suitable binding surface may include binding moiety, binding domain, binding region, binding motif or binding site etc. An example of a 'binding surface' may be TATA binding protein (TBP) contains a concave surface that interacts specifically with TATA promoter elements and convex surface mediates protein-protein interactions with general and gene specific transcription factors.

The term "binding target" or "target molecule" refers to any agent that may be bound by a two-helix binder. A binding target may include one or more of peptides, proteins (e.g., antibodies), nucleic acids (e.g., polynucleotides, DNA, RNA, or aptamers); polysaccharides (e.g., lectins or sugars), lipids, enzymes, enzyme substrates, ligands, receptors, antigens, or haptens. The target may include a discrete chemical moiety or a three-dimensional structural component (e.g., 3D structures that arises from peptide folding).

A "cloning vector" is a nucleic acid molecule, for example, a plasmid, cosmid, or bacteriophage that has the capability of replicating autonomously in a host cell. Cloning vectors typically contain (i) one or a small number of restriction endonuclease recognition sites at which foreign DNA sequences can be inserted in a predictable fashion without loss of an essential biological function of the vector, and (ii) a marker gene that is suitable for use in the identification and selection of cells transformed or transfected with the cloning vector. Marker genes include genes that provide tetracycline resistance or ampicillin resistance, for example. The term vector refers to any autonomously replicating or integrating agent, including but not limited to plasmids, cosmids, and viruses (including phage), comprising a nucleic acid molecule to which one or more additional nucleic acid molecules may be added.

The terms "conservative variant" and "conservative variants" used herein apply to both amino acid and nucleic acid sequences. With respect to particular nucleic acid sequences, conservative variants refer to those nucleic acids that encode identical or similar amino acid sequences and include degenerate sequences. For example, the codons GCA, GCC, GCG, and GCU all encode alanine. Thus, at every amino acid position where an alanine is specified, any of these codons may be used interchangeably in constructing a corresponding nucleotide sequence. The resulting nucleic acid variants are conservatively modified variants, since they encode the same protein (assuming that is the only alteration in the sequence). One skilled in the art recognizes that each codon in a nucleic acid, except for AUG (sole codon for methionine) and UGG (tryptophan), may be modified conservatively to yield a functionally identical peptide or protein molecule.

As to amino acid sequence substitutions, deletions, or additions to a polypeptide or protein sequence that alter, add or delete a single amino acid or a small number typically less than about 10% of amino acids is a "conservative variant" where the alteration results in the substitution of an amino acid with a chemically similar amino acid. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine.

The term "covalent bridge" or "covalent bridge of staple" used herein to describe a type of cross-linking between two different residues having electrons to share and form a covalent bond. A number of approaches for covalent helix stabilization have been reported, for example using cross-links such as disulfide links or lactum bridges. Olefenic cross-linking of helices through O-allyl substituted residues located on adjacent helical turns may also be made using ruthenium-catalysed ring closing metathesis. The configuration of cross-links differs in position of attachment, stereochemistry and its arm length, where some configuration imparts helix-stabilization.

"Cysteine" and "methionine" are two 'sulfur containing amino acids'. Cysteine is a thiol-containing amino acid that involves in active sites and protein tertiary structure determination. Cysteine also stabilizes proteins by forming intramolecular or intermolecular disulfide bond formation.

The term "extended cysteine" or "homocysteine" which is an unnatural amino acid derivative analogous to the naturally occurring cysteine but with an extra methyl group in the side-chain expected to bestow more flexibility relative to the side chain of naturally occurring cysteine. This cysteine homologue is called "extended" cysteine in some embodiments.

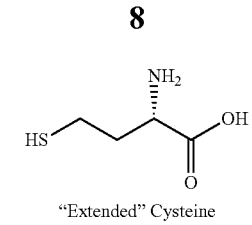

"Extended" Cysteine

The term "hindered" cysteine or "penicillamine" refers to cysteine derivatives with two methyl groups attached to the β carbon of the side-chain. One representative example of a hindered cysteine is penicillamine.

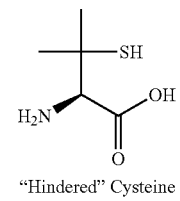

"Hindered" Cysteine

The term "poor helix formers" refers to amino acid residues with a propensity to disrupt the structure of alpha helices when contained at internal positions within the helix. Ala (A), Glu (E), Lys (K), Leu (L), Met (M), and Arg (R) are good alpha-helix formers, while Pro (P), Gly (G), Tyr (Y), and Ser (S) are poor alpha-helix formers. However, all poor alpha helix formers have been successfully substituted into the binding interface of the Z domain scaffold while still retaining binding affinity for a target. Of these residues, Pro (P) is not preferred for substitution of residues within a helix because of its rigid structure. Furthermore, D-amino acids may disrupt helical structure when contained in a L-peptide and, likewise, L-amino acids disrupt helical structure when contained in a D-peptide. Thus, in some embodiments, the amino acids comprising the two helix binder polypeptides substantially consist of amino acids of a single isomeric orientation (i.e., mostly D-peptides or mostly L-peptides).

The term "helix promoting amino acid" refers to an amino acid that has a high propensity to promote alpha helix formation of an amino acid sequence containing such amino acids. It is known in the art that naturally occurring amino acids, which are helix-promoting amino acids include glutamic acid, alanine, leucine, methionine, glutamine, isoleucine, lysine, arginine, histidine, phenylalanine, tryptophan and non-naturally occurring amino acid such as an amino butyric acid (e.g. alpha-amino isobutyric acid). The term "helix promoting", when used herein, is customarily referring to the effect of one or more amino acid substitutions on contributing to the helicity of a peptide, and more particularly an effect observed as one or more alpha helix stabilizing, or increase in helicity, as known in the art.

"Hydrophilic Amino Acid" refers to an amino acid exhibiting a hydrophobicity of less than zero according to the normalized consensus of the Eisenberg hydrophobicity scale. Genetically encoded hydrophilic amino acids include Thr (T), Ser (S), His (H), Glu (E), Asn (N), Gln (O), Asp (D), Lys (K), and Arg (R).

"Hydrophobic Amino Acid" refers to an amino acid exhibiting a hydrophobicity of greater than zero according to the normalized consensus hydrophobicity Eisenberg scale. Genetically encoded hydrophobic amino acids include Pro (P), Ile (I), Phe (F), Val (V), Leu (L), Trp (W), Met (M), Ala (A), Gly (G) and Tyr (Y).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded apolar amino acids include Leu (L), Val (V), Ile (I), Met (M), Gly (G), and Ala (A).

"Polar Amino Acid" refers to a hydrophilic amino acid having a side chain that is uncharged at physiological pH, but which has at least one bond in which the pair of electrons shared in common by two atoms is held more closely by one of the atoms. Polar amino acids include Asn (N), Gln (O), Ser (S), and Thr (T).

As used herein, the terms "protein", "peptide" and "polypeptide" are used herein to describe any chain of amino acids, regardless of length or post-translational modification (for example, glycosylation or phosphorylation). Thus, the terms may be used interchangeably herein to refer to a polymer of amino acid residues. The terms also apply to amino acid polymers in which one or more amino acid residue is an artificial chemical mimetic of a corresponding naturally occurring amino acid. Thus, the term "polypeptide" includes full-length, naturally occurring proteins as well as recombinantly or synthetically produced polypeptides that correspond to a full-length naturally occurring protein or to particular domains or portions of a naturally occurring protein. The term also encompasses truncated proteins as well as short peptide sequences. Further, the term "polypeptide" refers to synthetic and naturally occurring polypeptides known in the art. Although, the polypeptide targets may be of any length, suitable polypeptides include those comprising at least 3 amino acid residues, at least comprising 10 amino acid residues, at least 25 amino acid residues, or at least 100 amino acid residues.

As used herein the term "sample" refers to biological material that can be selected from cell culture, tissue culture, tissue section, biopsy, body fluid, tumor, cryosection, or cell smear. The sample can be derived from diseased individual or a healthy individual.

The term "scaffold" with reference to helical binders generally refers to those residues of the two helix binder polypeptide that provides the three-dimensional structure to adequately position the binding interface residues of the polypeptide such that binding to a target is enabled. Specifically, residues 2 through 14 of the first alpha helix and residues 20 through 32 of SEQ ID NO.:2 of the second alpha helix contribute to the helical segment of the two helix binder scaffold and residues 15 through 19 contribute to a loop segment of the two helix binder scaffold thereby effecting the relative orientation of the helices and binding to target of SEQ ID NO.:2. Residues 1 through 5 and 37 through 39 of SEQ ID NO. 4 contribute to non-helical termini, which may also contribute to proper orientation of the helices.

As used herein, the term "signal generator" refers to a molecule capable of providing a detectable signal using one or more detection techniques including, for example, spectrometry, calorimetry, spectroscopy, or visual inspection. Suitable examples of signal generators may include a chromophore, a fluorophore, a Raman-active tag, a radioactive label, an enzyme, an enzyme substrate, or combinations thereof. Suitable examples of a detectable signal may include an optical signal, and electrical signal, or a radioactive signal. In some instances the signal generator and the binder are present in a single entity (e.g., a target binding protein with a fluorescent label or radiolabel). And, in other instances the binder and the signal generator are discrete entities (e.g., target receptor protein and antibody against that particular receptor protein) that associate with each other following introduction to the sample.

Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

EMBODIMENTS

In general, the two helix binders provided herein may be used to perform the functions that other binders (e.g., antibodies) are used to perform. Thus, the two helix binders may be used, for example, as capture agents (e.g., an affinity selection agent) or as detection agents (e.g., an ELISA agent). When used as detection agents the two helix binders may be modified to generate a signal by the addition of a label (e.g., a fluorophore or a radioisotope). When used as capture agents, the two helix binders may be modified to include a tag (e.g., a his tag) that enhances the ability to the two helix binder to bind to an affinity column.

The two helix binding polypeptides may be generated using standard solid phase synthesis techniques, for example, as described below in Example 1. Alternatively, the polypeptides may be generated using recombinant techniques. In embodiments where the polypeptides are generated using recombinant techniques, the DNA encoding the polypeptides or conservative variants thereof may be isolated. The DNA encoding the polypeptides or conservative variants thereof may be inserted into a cloning vector, introduced into a host cell (e.g., a eukaryotic cell, a plant cell, or a prokaryotic cell), and expressed using any art recognized expression system.

Whether the polypeptide is generated using peptide synthesis techniques or recombinant techniques, the polypeptides generated may be substantially comprised of a single chiral form of amino acid residues. Thus, polypeptides of the invention may be substantially comprised either L-amino acids or D-amino acids; although a combination of L-amino acids and D-amino acids may also be employed.

As the polypeptides provided herein are derived from the Z-domain of protein A (SEQ. ID. NO. 1), residues on the binding interface may be non-conservatively substituted or conservatively substituted while preserving binding activity. In some embodiments, the substituted residues may be any of the 20 naturally occurring amino acids or any of analog thereof.

The two helix binders provided herein consist essentially of polypeptides approximately 39 residues in length. The length of the polypeptides may be about 28 residues to about 41 residues or about 30 to about 35 amino acids.

Additional sequence may be added to the termini to impart selected functionality. Thus, additional sequences may be appended to one or both termini to facilitate purification or isolation of a two helix binder, alone or coupled to a binding target (e.g., by appending a his tag to the polypeptide). A signal generator may be incorporated into the polypeptide at terminal position or at an internal position. Suitable examples of signal generators may include a chromophore, a fluorophore, a Raman-active tag, a radioactive label, an enzyme, an enzyme substrate, or combinations thereof. Suitable examples of a detectable signal may include an optical signal, and electrical signal, or a radioactive signal. In some instances the signal generator and the binder are present in a single entity (e.g., a target binding protein with a fluorescent label or radiolabel). And, in other embodiments the binder and the signal generator are discrete entities (e.g., target receptor protein and antibody against that particular receptor protein) that associate with each other following introduction to the sample.

A linker moiety may be appended to the polypeptide to facilitate linkage to a separate chemical entity (e.g., a tag or a label). The two helix binder polypeptides disclosed herein may be further modified to enhance pharmokinetics (e.g., by appending polyglycans to modulate blood circulation half life).

The polypeptides provided herein may be comprised of naturally occurring amino acids and analogues of naturally occurring amino acids. In some embodiments, the polypeptides may contain a single enantiomer of an amino acid residue. In alternative embodiments, the polypeptides may contain a combination of D- and L-forms of amino acids.

Methods available for substitution of amino acids include mutagenesis of the cDNA encoding the described polypeptide by a number of methods known to those skilled in the art, including random mutagenesis, site-directed mutagenesis, and mutagenesis using error prone PCR. A preferred method to introduce random substitutions into the binding interface positions is the use of DNA containing degenerate primers (e.g., NNK) at the codons of desired substitution.

Substitutions of residues in either the polypeptide provided herein with prolines or cysteines are generally disfavored. However, prolines and cysteines may occur in the polypeptides of the invention under certain conditions.

Proline, as a poor helix former is generally disfavored. However, Z-domain polypeptides containing prolines are known to be capable of binding target. Consequently, proline substitutions in the scaffold portions of the polypeptide are not absolutely prohibited, but should be limited to less than about 20% of the total scaffold residues. Similarly, proline substitutions in the binding interface are also disfavored but are permitted.

Cysteine residues may form intermolecular or intramolecular disulfide bridges with other cysteine residue. Therefore, other than the cysteine residues and their positions in the two helix binders disclosed herein, additional cysteines are not preferred, especially if more than one, as unwanted disulfide formation and structural changes may occur. An exception to this scenario may be when an additional thiol moiety via a cysteine is desired to form a dimer of the two helix binder by an intermolecular disulfide formation.

Although cysteine substitutions within the binding interface are generally disfavored, in some embodiments, residues in the binding interface may be substituted with cysteine residues under certain conditions. Thus, if a non-cysteine residue is replaced with cysteine residues, the substitution is preferably replaced in two positions such that the thiol reactive group in the pair of substituted cysteine residues that are positioned to permit formation of a disulfide bridge to enhance stability of a helix. The substitution of cysteine in pairs that are capable of forming disulfide bridges further avoids disfavored constructs in which an unpaired reactive thiol group is present in the polypeptide.

Similarly, although a proline substitution within the binding interface is generally disfavored, in some embodiments, residues in the binding interface may be substituted with proline under certain conditions. Thus, if proline residues are substituted in the polypeptides, the total number of proline substitutions should be limited to less than about 10% of the total number of residues in the polypeptide.

For an amino acid identified for a position in the two helix binder in the polypeptide shown in Table 1 to obtain binding to a target, conservative changes are permitted (e.g., one polar amino acid may potentially be substituted for another polar residue). Non-conservative changes are also permitted in the binding interface, but only if improvement in binding occurs.

In general, a single amino acid should not comprise more than about 60% of the total number of interface amino acids. In embodiments where the target comprises multiple repeat structures (e.g., collagen) more than 60% of a single amino acid may be allowed in the binding interface.

Although, the scaffold portions of the polypeptides are preferred to be unchanged so as to preserve the two helix binding conformation, conservative and non-conservative mutations in scaffold residues that do not result in a loss of binding are permitted wherein the total non-conservative substitutions being restricted to fewer than about 20% of the total number of helical portions of the scaffold. In general, substitutions of proline residues are disfavored, but are not strictly prohibited. An exemplary 39 residue two helix polypeptide is provided in Table 1 below, in which generally favored and disfavored substitutions are indicated.

TABLE 1

| Amino Acid (SEQ ID NO: 44) | Function | Favored Substitutions | Disfavored Substitutions |
|---|---|---|---|
| V | Scaffold, terminus | Cys | None |
| $X_1$ | Scaffold, terminus | Cys | None |
| N | Scaffold, terminus | Cys | None |
| K | Scaffold, terminus | Cys | None |
| F | Scaffold, terminus | Cys, Conserved | Non-conserved |
| N | Scaffold, helix | Cys, Conserved | Non-conserved |
| K | Scaffold, helix | Cys, Conserved | Non-conserved |
| E | Scaffold, helix | Cys, Conserved | Non-conserved |
| $X_2$ | Binding Interface | ADEFGHIKLMNPQRSTVW | Cys, Pro |
| $X_2$ | Binding Interface | ADEFGHIKLMNPQRSTVW | Cys, Pro |
| $X_2$ | Binding Interface | ADEFGHIKLMNPQRSTVW | Cys, Pro |
| A | Scaffold, helix | Conserved | Non-conserved |
| $X_2$ | Binding Interface | ADEFGHIKLMNPQRSTVW | Cys, Pro |
| $X_2$ | Binding Interface | ADEFGHIKLMNPQRSTVW | Cys, Pro |
| E | Scaffold, helix | Conserved | Non-conserved |

TABLE 1-continued

| Amino Acid (SEQ ID NO: 44) | Function | Favored Substitutions | Disfavored Substitutions |
|---|---|---|---|
| I | Scaffold, helix | Conserved | Non-conserved |
| X$_2$ | Binding Interface | ADEFGHIKLMNPQRSTVW | Cys, Pro |
| X$_2$ | Binding Interface | ADEFGHIKLMNPQRSTVW | Cys, Pro |
| L | Scaffold, loop | Conserved | Non-conserved |
| P | Scaffold, loop | None | Non-conserved |
| N | Scaffold, loop | Conserved | Non-conserved |
| L | Scaffold, loop | Conserved | Non-conserved |
| N | Scaffold, loop | Conserved | Non-conserved |
| X$_2$ | Binding Interface | ADEFGHIKLMNPQRSTVW | Cys, Pro |
| X$_2$ | Binding Interface | ADEFGHIKLMNPQRSTVW | Cys, Pro |
| Q | Scaffold, helix | Conserved | Non-conserved |
| X$_2$ | Binding Interface | ADEFGHIKLMNPQRSTVW | Cys, Pro |
| X$_2$ | Binding Interface | ADEFGHIKLMNPQRSTVW | Cys, Pro |
| A | Scaffold, helix | Conserved | Non-conserved |
| F | Scaffold, helix | Conserved | Non-conserved |
| I | Scaffold, helix | Conserved | Non-conserved |
| X$_2$ | Binding Interface | ADEFGHIKLMNPQRSTVW | Cys, Pro |
| S | Scaffold, helix | Conserved | Non-conserved |
| L | Scaffold, helix | Conserved | Non-conserved |
| X$_2$ | Binding Interface | ADEFGHIKLMNPQRSTVW | Cys, Pro |
| D | Scaffold, helix | Cys, Conserved | Non-conserved |
| D | Scaffold, terminus | Cys, Conserved | Non-conserved |
| P | Scaffold, terminus | Cys | None |
| S | Scaffold, terminus | Cys | None |

In general, the two helix binders provided herein demonstrate a binding affinity for the target in the range of about 50 nM to about 200 nM. The anti-IgG two helix binder described below in the Examples (SEQ ID NO.:7) has demonstrated an affinity of about 50 nM for its target, IgG. The anti-HER2 two helix binder described in the Examples below (SEQ ID NO.: 8) has demonstrated an affinity of about 150 nM for its target, HER2.

It is desirable to have polypeptides having fewer alpha helices with enhanced binding efficiencies. It is also desirable to have small polypeptides that can specifically bind to the targets easily. Some embodiments of the present invention describe polypeptides isolated from Z-domain of *Staphylococcal* protein A, which contains 2-alpha helices and a binding surface. Some embodiments describe methods for binding a target using the described polypeptides. In some embodiment, the target of two helix binder is also described as HER2 and EGFR.

One or more embodiments of the present inventions describe the modifications introduced into the two helix polypeptides. The advantage of these modifications is to stabilize the isolated polypeptide and to increase the binding efficiency towards the target molecules. This modification may be one or more substitution by natural or unnatural amino acids or may be an introduction of engineered bridge between two different amino acids or amino acid analogs in the scaffold.

The stabilization of the polypeptide scaffold can be done by different changes like, introduction of a covalent bridge, formation of an engineered disulfide linkage, substitution of an unnatural helix promoting amino acid or natural amino acids for scaffold modifications.

In some embodiments, the present invention provides a polypeptide scaffold containing two helices that may stabilize with a covalent bridge formed between two unnatural amino acid residues. In some embodiments, the covalent bridge may increase the affinity of the polypeptide to bind various targets. Some embodiments have a covalent bridge that connects or extends two non-natural amino acids. In these embodiments, "connects" or "extends" means two non-natural amino acids are connected or bridged or linked by a covalent bond.

In some embodiments, the polypeptide scaffold includes an engineered disulfide bridge formed between two unnatural cysteine analogs. In some embodiments, the engineered disulfide bridge may increase the affinity of the peptide to bind various targets. In some other embodiments, the engineered disulfide bridge may provide stability to the polypeptide scaffold. Some embodiments have a disulfide bond that connects or extends two natural or non-natural cysteine residues. In these embodiments, "connects" or "extends" means two natural or non-natural cysteines are connected or bridged or linked by a disulfide bond.

In some embodiments, the present invention provides an amino acid scaffold containing two helices that is stabilized with unnatural amino acid (or non-natural) or its analog. In some embodiment, the unnatural amino acid or its analog may be a helix promoting amino acid. In some other embodiment, the unnatural amino acid or its analog may increase the affinity of the polypeptide to bind different targets such as Her2 or EGFR.

In some embodiments the present invention describes a polypeptide scaffold containing two helices that may stabilize with natural amino acid mutations. The natural amino acid mutations may also increase the affinity of the polypeptide to bind various targets like Her2 or EGFR.

The polypeptide scaffold may be used to perform any of the functions that other binders (e.g., antibodies) do. Thus, the two helix binder may be used, for example, as capture agents (e.g., an affinity selection agent) or as detection agents (e.g., an ELISA agent). When used as detection agents the two helix binder may be modified to generate a signal by the addition of a label (e.g., a fluorophore or a radioisotope). When used as capture agent, the two helix binder may be modified to include a tag (e.g., a his tag) that enhances the ability to the two helix binder to bind to an affinity column. This peptide may be useful in targeting drug where it can be served as a control to measure the efficiency of drug.

Whether the two helix binder is generated using peptide synthesis techniques or recombinant techniques, the polypeptides generated may be substantially comprised of a single chiral form of amino acid residues. Thus, two helix binder of the invention may be substantially comprised either L-amino acids or D-amino acids; although a combination of L-amino acids and D-amino acids may also be employed.

In some embodiments, additional sequence may be added to the termini to impart selected functionality. Thus, additional sequences may be appended to one or both termini to facilitate purification or isolation of a two helix binder, alone or coupled to a binding target (e.g., by appending a his tag to the polypeptide). A signal generator may be incorporated into the polypeptide at terminal position or at an internal position. Suitable examples of signal generators may include a chromophore, a fluorophore, a Raman-active tag, a radioactive label, an enzyme, an enzyme substrate, or combinations thereof. Suitable examples of a detectable signal may include an optical signal, and electrical signal, or a radioactive signal. In some instances the signal generator and the binder are present in a single entity (e.g., a target binding protein with a fluorescent label or radiolabel). And, in other embodiments the binder and the signal generator are discrete entities (e.g., target receptor protein and antibody against that particular receptor protein) that associate with each other following introduction to the sample. In some embodiments the signal generator may be attached to the polypeptide. In some embodiments, the attachment may be a physical attachment. In some other embodiments, the attachment may be a chemical attachment.

The two helix binders provided herein may be comprised of naturally occurring amino acids and analogs of naturally occurring amino acids. In some embodiments, the two helix binder may contain a single enantiomer of an amino acid residue. In alternative embodiments, the polypeptides may contain a combination of D- and L-forms of amino acids.

Methods available for substitution of amino acids include mutagenesis of the cDNA encoding the described polypeptide by a number of methods known to those skilled in the art, including random mutagenesis, site-directed mutagenesis, and mutagenesis using error prone PCR. A preferred method to introduce random substitutions into the binding interface positions is the use of DNA containing degenerate primers (e.g., NNK) at the codons of desired substitution.

In some embodiments, the method of introducing covalent bridge is discussed, wherein two allyl amino acids placed in (i–i+7) positions and were subjected to ring closing metathesis using Grubbs catalyst.

Although cysteine substitutions within the binding interface are generally disfavored, in some embodiments, residues in the binding interface may be substituted with cysteine residues under certain conditions. The substitution of cysteine in pairs that are capable of forming disulfide bridge further avoids disfavored constructs in which an unpaired reactive thiol group is present in the polypeptide.

A disulfide linkage between two helix binders increases the stability of the molecule. In some cases this linkage add rigidity to the molecule depending on its structure. In some embodiments, the stability of the scaffold may increase by modifying the disulfide linkage on introduction of a cysteine analog at the terminal position of that linkage.

The optimal position of the disulfide bond in two helix binder is determined. The positions of the cysteine residues are changed around positions 5 and 39, but also moved the disulfide linkage along the axis of the two helices forming pairs between residues 9 and 34, 9 and 35, 13 and 30, 13 and 31, 16 and 27, 17 and 27. For disulfides at the axis location similar to that of peptide of SEQ. ID. NO. 21, relative binding studies by SPR (Surface Plasmon Resonance) showed that the original placement of the bond is indeed optimal.

In some embodiments, a number of unnatural analogs of cysteine amino acid are used. Such mutants allowed the utilization of the thiol chemistry developed to cyclize the truncated two-helix. Homocysteine is an unnatural amino acid derivative analogous to the naturally occurring cysteine but with an extra methyl group in the side-chain expected to bestow more flexibility relative to the side chain of naturally occurring cysteine. This cysteine analog is an extended cysteine. The cysteine derivative penicillamine has two methyl groups attached to the beta carbon of the side-chain and is more sterically hindered. This cysteine analog is called "hindered" cysteine. All combinations between the extended or hindered side-chain-containing cysteine variants and natural cysteine and the combinations between extended and hindered cysteines are studied. Using SPR, relative binding studies identifies the variant containing two extended linkers to have the highest affinity.

In some embodiments, the binding affinity of two helix polypeptide may increase in case of introducing two homocysteines or "extended" cysteines in both of the terminal positions of the disulfide linkage. It may reduce steric hindrance that results better fitting of the peptide to the binding surface of the target molecule. The disulfide bond between hindered cysteines is not favored because of its bulky structure.

Helix promoting amino acids are well known in the literature and such amino acids could rigidify the 2-helix construct. Aminoisobutyric acid (Aib) promotes alpha-helix formation. The positions 8, 12 and 16 on the N-terminal helix and positions 26, 30 and 34 on the C-terminal helix are identified as possible sites for mutation to Aib in the construct.

Figure 1:
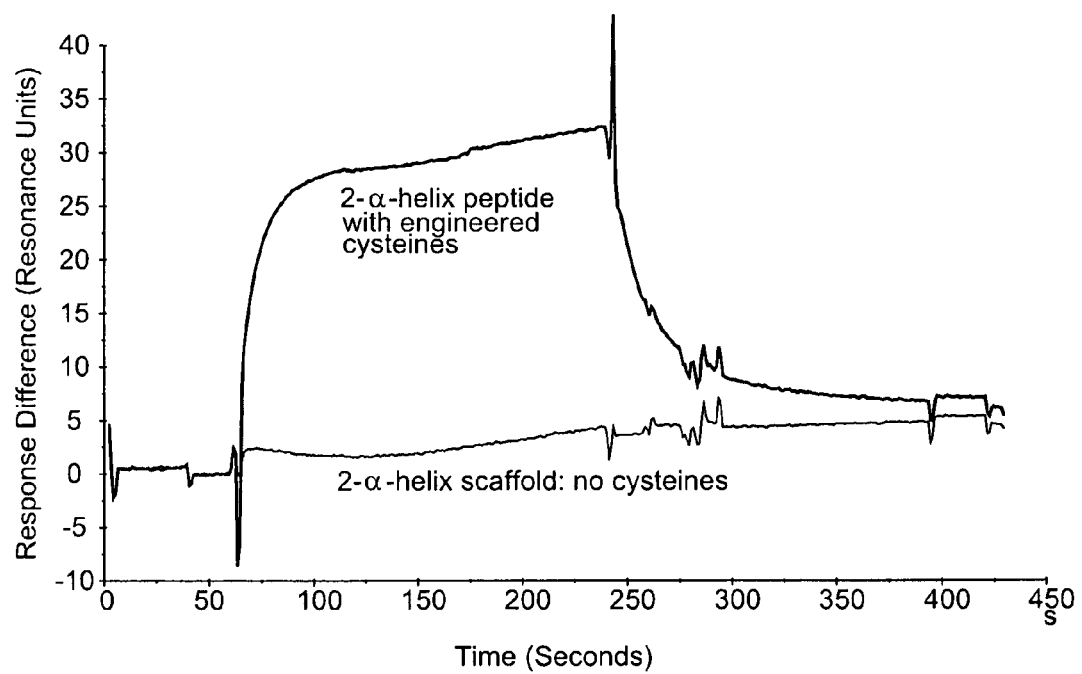
Figure 2:
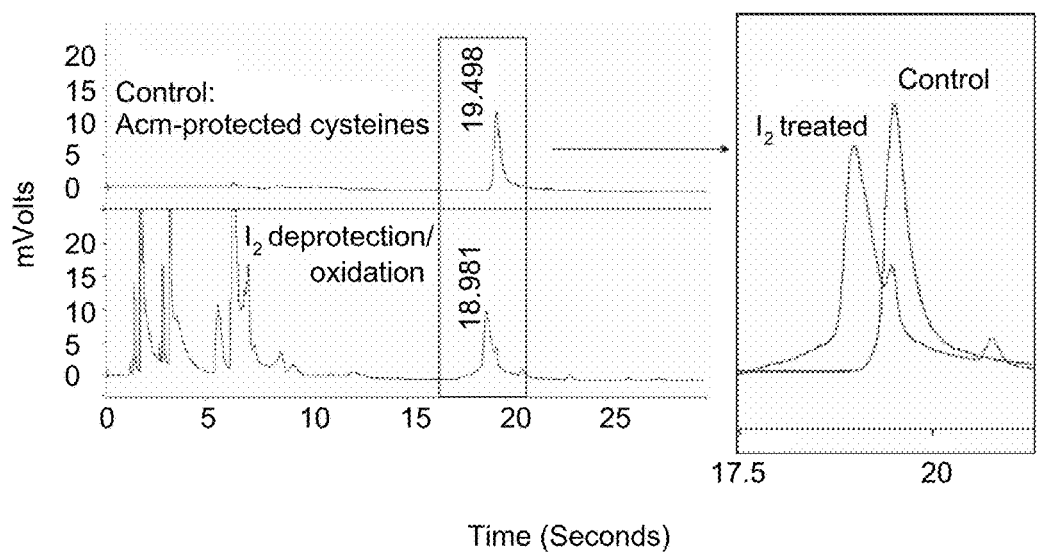
Figure 3:
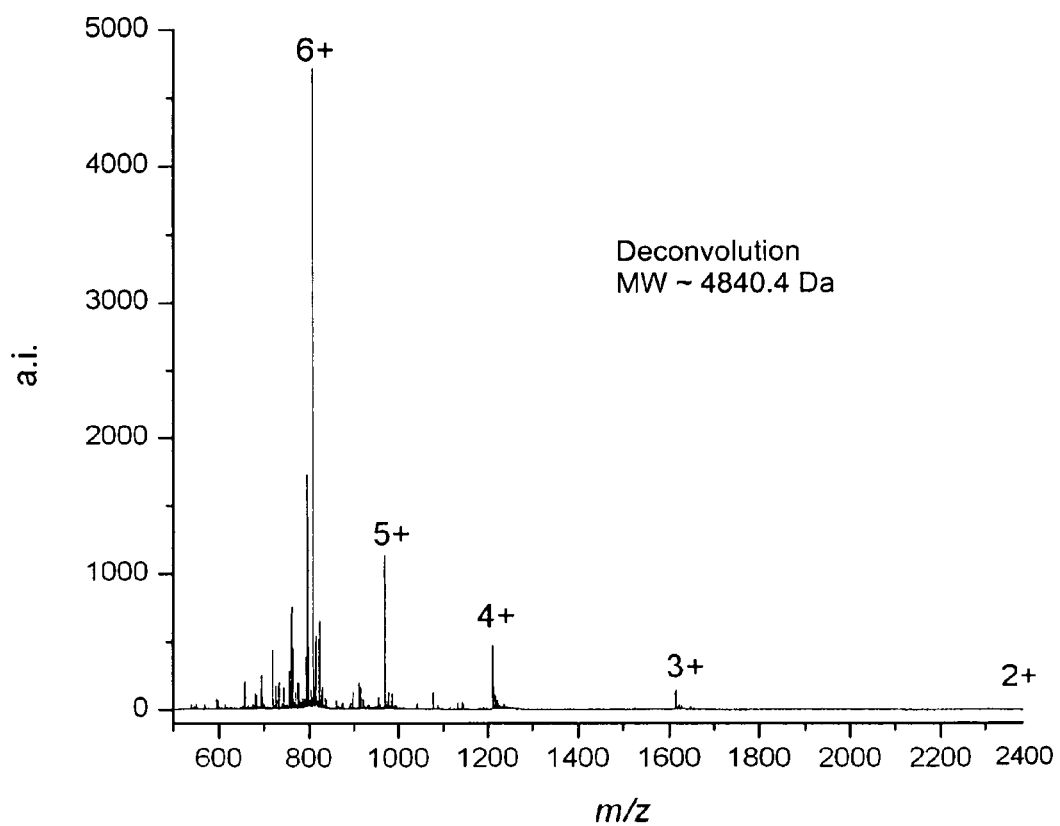
Figure 4:
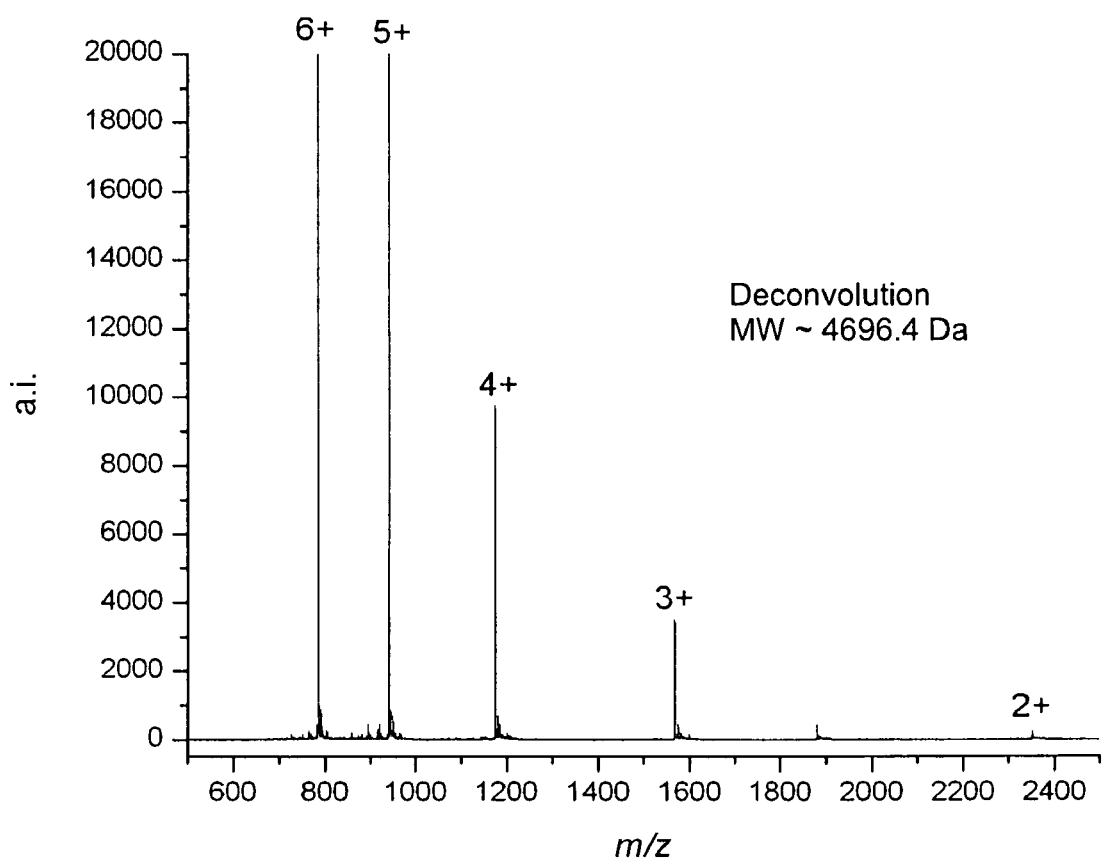
Figure 5:
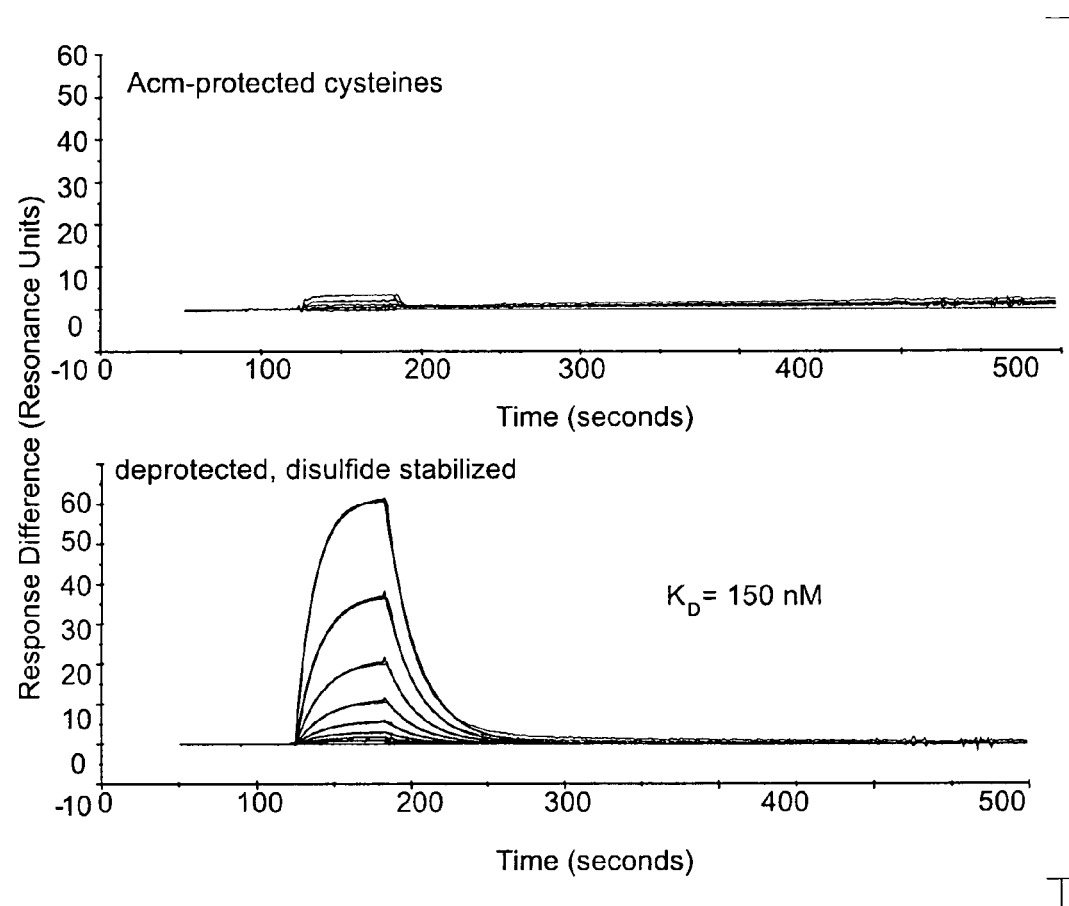
Figure 6:
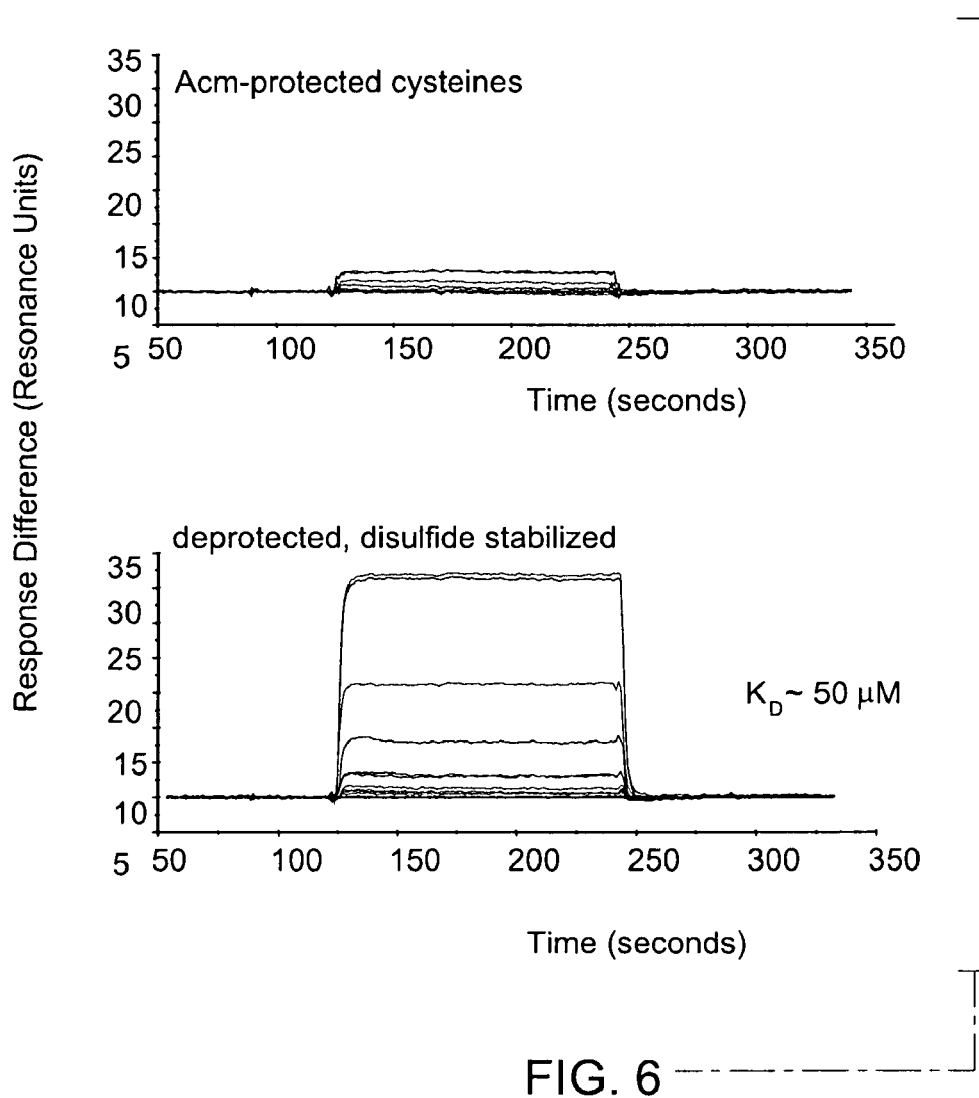
Figure 7A:
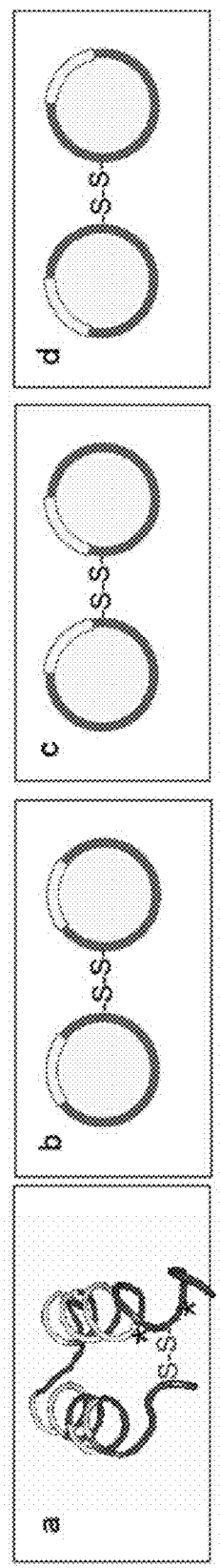
FIG. 7C shows the relative binding analysis of these ihree peptides to Her2 shows that altering the site of disulfide bond formation results in a corresponding change in affinity for the target.
Figure 7C:
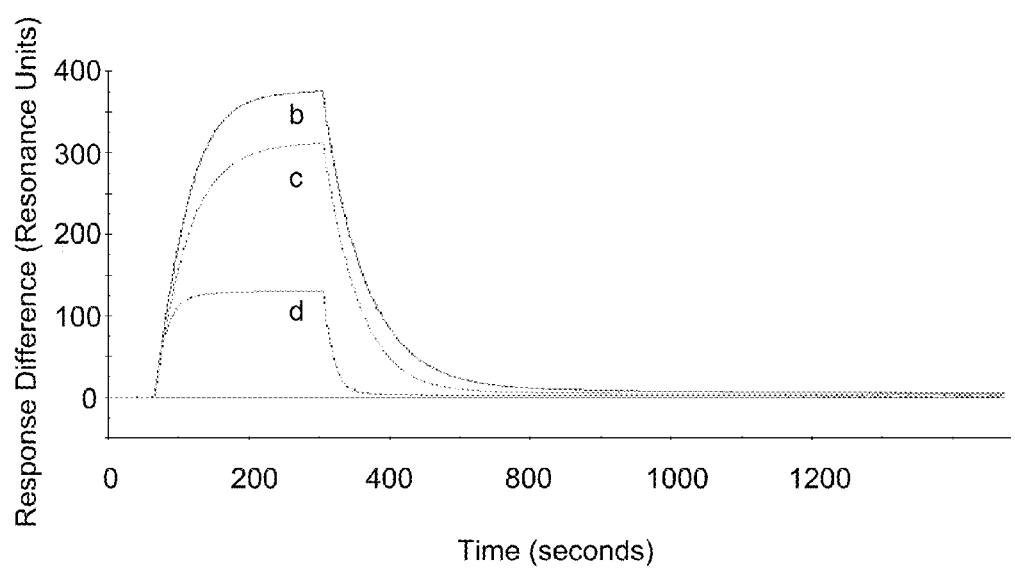
Figure 8:
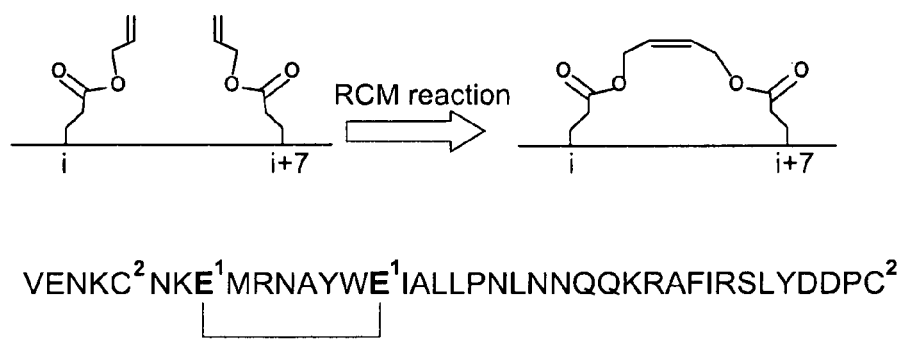
FIG. 8 depicts the schematic presentation of ring closure metathesis reaction and a polypeptide (SEQ ID NO: 43) stabilized with a covalent bridge.

G29A substitution (substitution of alanine (A) in place of glycine (G) at 29th position of the sequence) in Z-domain of protein A significantly stabilizes the second helix and increases the rate of folding. In some embodiments, the polypeptide of SEQ. ID. NO. 24 is provided wherein Aib is incorporated at 8th, 12th and 16th positions in N-terminal helix; the polypeptide of SEQ. ID. NO. 25 is provided wherein Aib is incorporated at 26th, 30th and 34th positions in C-terminal helix and the polypeptide of SEQ. ID. NO. 26 is provided wherein Aib is incorporated at all six positions such as $8^{th}$, $12^{th}$ $16^{th}$, $26^{th}$, $30^{th}$ and $34^{th}$, the helicity increases for all three variants but they are unable to bind target molecule. The polypeptide of SEQ. ID. NO. 27 is provided, wherein, substitution of only one Aib in the place of alanine at the $29^{th}$ position increases its binding affinity for the target molecule. The schematic presentation of the polypeptide of SEQ. ID. NO. 12, having a covalent bridge between two un-natural amino acids is also described in FIG. 8. In some embodiments, a covalent bridge is formed between two $E^1$ (o-allyl glutamic acid or its analog) residues that stabilizes the peptide and increases its binding affinity.

(SEQ ID NO: 12)

VENKCNKE$^1$MRNAYWE$^1$IALLPNLNNQQKRAFIRSLYDDPC

In some embodiments, the substitution of alpha amino isobutyric acid (Aib) in SEQ. ID. NO. 27 stabilizes the peptide and increases its binding affinity. In some other embodiments, the substitution of A12R, I16A, L19D, F30K and L34I in SEQ. ID. NO. 28 stabilizes the peptide and increases its binding affinity.

The schematic presentation of a polypeptide of SEQ. ID. NO. 18, having a disulfide linkage between two natural or un-natural cystein or its analogs is depicted below. The disulfide bond (or linkage) stabilizes the peptide and increases its binding affinity.

(SEQ ID NO: 41)

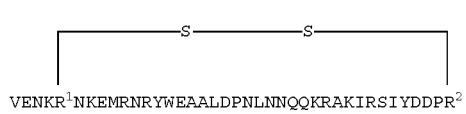

VENKR$^1$NKEMRNRYWEAALDPNLNNQQKRAKIRSIYDDPR$^2$

In other embodiments, a signal generator may be attached to the isolated polypeptide. The signal generator may include, but is not limited to, a fluorescent or a radioactive or a paramagnetic probe or combinations thereof. In some embodiments, a non-limiting example of a fluorescent probe is a pH sensitive cyanine dye. In some embodiments the radioactive probe may include, but is not limited to, C11, F18, P32, Tc99m, $Cu^{+2}$ or $Ga^{+2}$ or a combination thereof.

One of the methods of identifying a target in a sample comprises the steps of contacting the polypeptide with the sample, observing a signal produced by the signal generator, and identifying the presence or absence of target by the observed signal generated from the sample. The target molecule may be further identified in a control sample that comprises the steps of contacting the polypeptide with the control sample, observing a signal produced by the signal generator in the control sample and finally qualitatively or quantitatively comparing the signal produced from the test sample with the control sample. The sample may comprise, but is not limited to, histological samples, cell cultures, biopsied materials, or tissue sections.

In some embodiments, the four-residue N-terminal truncated variant of (SEQ ID NO: 30)
VENKCNKE$^1$MRNAYWE$^1$IALLPNLNNQQKRXFIRSLYDDPC is (SEQ ID NO: 42)
CNKE$^1$MRNAYWE$^1$IALLPNLNNQQKRXFIRSLYDDPC.

is

The combination of four strategies such as incorporation of engineered disulfide linkage, formation of covalent linkage between two modified amino acids, substitution of amino acid by unnatural amino acid or its analogue and substitution by natural amino acid may contribute most significantly on the affinity of the 2-helix binder for Her2 or EGFR. In some embodiments, a polypeptide of SEQ. ID. NO. 32 is provided having the five natural amino acid sequence mutations, wherein the mutations are selected from a group where, alanine at position 12 is substituted by an arginine, isoleucine at position 16 is substituted by alanine; leucine at position 19 is substituted by aspartic acid; phenylalanine at position 30 is substituted by lysine; and leucine at position 34 is substituted by isoleucine (A12R, I16A, L19D, F30K and L34I); unnatural amino acid like Aib substitutions, and introduction of a disulfide bridge between two extended cysteine residues along with covalent bridge between two unnatural amino acids like O-allyl glutamic acids. In some embodiments, SPR analysis showed the peptide of SEQ. ID. NO. 32 has a binding affinity for HER-2 is of 5 nM. Circular Dichroism (CD) revealed this peptide have the highest population of helix conformers. This may suggest that a minimum amount of secondary structure is necessary to maintain its structural integrity and the structural motif of its binding site.

Table 2 below provides sequences referred to herein.

TABLE 2

| | | Residues |
|---|---|---|
| SEQ ID NO. 1 | protein A Z domain: VDNKFNKEQQNAFYEILHLPNLNEEQ RNAFIQSLKDDPSQSANLLAEAKKLN DAQAPK | 58 |
| SEQ ID NO. 2 | protein A: FNKEX$_2$X$_2$X$_2$AX$_2$X$_2$EIX$_2$X$_2$LPNLN X$_2$X$_2$QX$_2$X$_2$AFIX$_2$SLX$_2$DDPS; scaffold residues are shown as X2. | 35 |
| SEQ ID NO. 3 | N-terminus sequences: VX$_1$NK, wherein X$_1$ may be D or E: | 4 |
| SEQ ID NO. 4 | SEQ ID NO: 2 and SEQ ID NO. 3 combined, VX$_1$NKFNKEX$_2$X$_2$X$_2$AX$_2$X$_2$EIX$_2$X$_2$ LPNLNX$_2$X$_2$QX$_2$X$_2$AFIX$_2$SLX$_2$DDP S; wherein X$_1$ may be D or E: | 39 |
| SEQ ID NO. 5 | anti-IgG two helix binder: VX$_1$NKFNKEQQNAFYEILHLPNLNEE QRNAFIQSLKDDPS, wherein X$_1$ may be D or E. | 39 |
| SEQ ID NO. 6 | anti-Her2 two helix binder: VX$_1$NKFNKEMRNAYWEIALLPNLNNQ QKRAFIRSLYDDPS, wherein X$_1$ may be D or E. | 39 |
| SEQ ID NO. 7 | anti-IgG two helix binder: VENKCNKEQQNAFYEILHLPNLNEEQ RNAFIQSLKDDPC with C substitutions. | 39 |
| SEQ ID NO. 8 | anti-Her2 two helix binder: VENKCNKEMRNAYWEIALLPNLNNQQ KRAFIRSLYDDPC with C substitutions. | 39 |
| SEQ ID NO. 9 | anti-Her2 two helix binder: VENKFCKEMRNAYWEIALLPNLNNQQ KRAFIRSLYDDPC with C substitutions. | 39 |
| SEQ. ID. NO. 10 | anti-Her2 two helix binder: VENCFNKEMRNAYWEIALLPNLNNQQ KRAFIRSLYDDPC with C substitutions. | 39 |
| SEQ. ID. NO. 11 | a truncated sequence for the protein A Z domain: VENKFNKEMRNAYWEIALLPNLNNQQ KRAFIRSLYDDPG. | 39 |
| SEQ. ID. NO. 12 | anti-Her2 two helix binder: VENKCNKE$^1$MRNAYWE$^1$IALLPNLNN QQKRAFIRSLYDDPC; wherein E$^1$ may be O-allyl glutamic acid [(S)-5-(allyloxy)-2-amino-5-oxopentanoic acid] or its analog and a | 39 |

TABLE 2-continued

| | | Residues |
|---|---|---|
| | covalent bridge is formed by $E^1$ residues. | |
| SEQ. ID. NO. 13 | anti-Her2 two helix binder: VENKCNKE$^1$MRNAYWD$^1$IALLPNLNN QQKRAFIRSLYDDPC; wherein $E^1$ may be O-allyl glutamic acid [(S)-5-(allyloxy)-2-amino-5-oxopentanoic acid] or its analog; $D^1$ may be O-allyl aspartic acid [(S)-4-(allyloxy)-2-amino-oxobutanoic acid] or its analog a covalent bridge is formed between $E^1$ and $D^1$ residues: | 39 |
| SEQ. ID. NO. 14 | an anti-Her2 two helix binder: VENKCNKA$^1$MRNAYWA$^1$IALLPNLNN QQKRAFIRSLYDPC; wherein $A^1$ may be (2S)-Fmoc-2-amino-8-nonenoic acid or its analog and a covalent bridge may form between two $A^1$ residues. | 39 |
| SEQ. ID. NO. 15 | anti-Her2 two helix binder: VENKCNKEMRNAYWEIALLPNLNNQ $E^1$KRAFIRE$^1$LYDDPC; wherein $E^1$ may be O-allyl glutamic acid [(S)-5-(allyloxy)-2-amino-5-oxopentanoic acid] or its analog and a covalent bridge may form between two $E^1$ residues. | 39 |
| SEQ. ID. NO. 16 | anti-Her2 two helix binder: VENKCNKEMRNAYWEIALLPNLNNQ $E^1$KRAFIRD$^1$LYDDPC; wherein $E^1$ may be O-allyl glutamic acid [(S)-5-(allyloxy)-2-amino-5-oxopentanoic acid] or its analog; $D^1$ may be O-allyl aspartic acid [(S)-4-(allyloxy)-2-amino-4-oxobutanoic acid] or its analog and a covalent bridge may form between $E^1$ and $D^1$ residues. | 39 |
| SEQ. ID. NO. 17 | anti-Her2 two helix binder: VENKCNKEMRNAYWEIALLPNLNNQ $A^1$KRAFIRA$^1$LYDDPC; wherein $A^1$ may be (2S)-Fmoc-2-amino-8-nonenoic acid or its analog and a covalent bridge may form between two $A^1$ residues. | 39 |
| SEQ. ID. NO. 18 | anti-Her2 two helix binder: VENKR$^1$NKEMRNAYWEIALLPNLNNQ QKRAFIRSLYDDPR$^2$; wherein $R^1$ and $R^2$ may be natural cysteine or cysteine analog and a disulfide linkage may form between $R^1$ and $R^2$ residues. | 39 |
| SEQ. ID. NO. 19 | anti-Her2 two helix binder: VENKC$^1$NKEMRNAYWEIALLPNLNNQ QKRAFIRSLYDDPC; wherein, | 39 |
| | $C^1$ may be hindered cysteine (e.g., penicilla-min) and a disulfide linkage may form between C1 and C (natural cysteine) residues: | |
| SEQ. ID. NO. 20 | anti-Her2 two helix binder: VENKC$^2$NKEMRNAYWEIALLPNLNNQ QKRAFIRSLYDDPC; wherein, C2 may be extended cysteine (e.g., homo-cysteine) and a disulfide linkage may form between C2 and C (natural cysteine) residues. | 39 |
| SEQ. ID. NO. 21 | anti-Her2 two helix binder: VENKC$^2$NKEMRNAYWEIALLPNLNNQ QKRAFIRSLYDDPC$^2$; wherein, C2 may be extended cysteine (e.g., homo-cysteine) and a disulfide linkage may form between two residues. | 39 |
| SEQ. ID. NO. 22 | anti-Her2 two helix binder: VENKC$^1$NKEMRNAYWEIALLPNLNNQ QKRAFIRSLYDDPC$^2$; wherein, $C^1$ may be hindered cysteine (e.g., penicilla-min); $C^2$ may be extended cysteine (e.g., homo-cysteine) and a disulfide linkage may form between $C^1$ and $C^2$ residues. | 39 |
| SEQ. ID. NO. 23 | anti-Her2 two helix binder: VENKCNKEMRNAYWEIALLPNLNNQQ KRAFIRSLYDDPC$^1$; wherein, $C^1$ may be hindered cysteine [e.g., penicilla-min] and a disulfide linkage may form between $C^1$ and C (natural cysteine) residues. | 39 |
| SEQ. ID. NO. 24 | anti-Her2 two helix binder: VENKCNKXMRNXYWEXALLPNLNNQQ KRAFIRSLYDDPC; wherein, X may be an alpha amino iso-butyric acid (Aib) or its analog. | 39 |
| SEQ. ID. NO. 25 | anti-Her2 two helix binder: VENKCNKEMRNAYWEIALLPNLNNQX KRAXIRSXYDDPC; wherein, X may be an alpha amino iso-butyric acid (Aib) or an Aib analog. | 39 |
| SEQ. ID. NO. 26 | anti-Her2 two helix binder: VENKCNKXMRNXYWEXALLPNLNNQX KRAXIRSXYDDPC; wherein, X may be an alpha amino iso-butyric acid (Aib) or an Aib analog. | 39 |
| SEQ. ID. NO. 27 | anti-Her2 two helix binder: VENKCNKEMRNAYWEIALLPNLNNQQ | 39 |

TABLE 2-continued

| | | Residues |
|---|---|---|
| | KRXFIRSLYDDPC; wherein, X may be an alpha amino isobutyric acid (Aib) or an Aib analog. | |
| SEQ. ID. NO. 28 | anti-Her2 two helix binder: VENKCNKEMRNRYWEAALDPNLNNQQ KRAKIRSIYDDPC; wherein underlined residues on 12, 16, 19, 30 and 34 positions may be substituted with natural amino acids. | 39 |
| SEQ. ID. NO. 29 | anti-Her2 two helix binder: VENKC$^2$NKEMRNRYWEAALDPNLNNQ QKRAKIRSIYDDPC$^2$; wherein, the residues on 12, 16, 19, 30 and 34 positions may have preferred substitutions by natural amino acids (underlined) and wherein, C$^2$ may be extended cysteine (e.g., homocysteine). | 39 |
| SEQ. ID. NO. 30 | anti-Her2 two helix binder: VENKCNKE$^1$MRNAYWE$^1$IALLPNLNN QQKRXFIRSLYDDPC; wherein E$^1$ may be O-allyl glutamic acid [(S)-5-(allyloxy)-2-amino-5-oxopentanoic acid] or its analog and a covalent bridge may form between two E$^1$ residues; and wherein X may be an alpha amino isobutyric acid (Aib) or an Aib analog. | 39 |
| SEQ. ID. NO. 31 | anti-Her2 two helix binder: VENKCNKE$^1$MRNRYWE$^1$AALDPNLNN QQKRXKIRSIYDDPC; wherein E$^1$ may be O-allyl glutamic acid [(S)-5-(allyloxy)-2-amino-5-oxopentanoic acid] or its analog and a covalent bridge may form between two E$^1$ residues; X may be an alpha amino isobutyric acid (Aib) or an Aib analog; and residues on 12, 16, 19, 30 and 34 positions may be substituted with natural amino acids (underlined). | 39 |
| SEQ. ID. NO. 32 | anti-Her2 two helix binder: VENKC$^2$NKE$^1$MRNRYWE$^1$AALDPNLN NQQKRXKIRSIYDDPC$^2$; wherein E$^1$ may be O-allyl glutamic acid [(S)-5-(allyloxy)-2-amino-5-oxopentanoic acid] or its analog and a covalent bridge may form between two E$^1$ residues; X may be an alpha amino isobutyric acid (Aib) or Aib analog; the residues on 12, 16, 19, 30 and 34 positions may have preferred substitutions by natural amino acids (underlined) and C$^2$ may be extended cysteine (e.g., homocysteine) and a disulfide linkage may form between two residues. | 39 |
| SEQ. ID. NO. 33 | anti-Her2 two helix binder: VENKC$^2$NKEMRNAYWEIALLPNLNNQ QKRXFIRSLYDDPC$^2$; wherein, C$^2$ may be extended cysteine (e.g., homocysteine) and a disulfide linkage may form between two residues; and wherein, X may be an alpha amino isobutyric acid (Aib) or Aib analog. | 39 |
| SEQ. ID. NO. 34 | anti-Her2 two helix binder: VENKC$^2$NKE$^1$MRNAYWE$^1$IALLPNLN NQQKRXFIRSLYDDPC$^2$; wherein, C$^2$ may be extended cysteine (e.g., homocysteine) and a disulfide linkage may form between two residues; wherein E$^1$ may be O-allyl glutamic acid [(S)-5-(allyloxy)-2-amino-5-oxopentanoic acid] or its analog and a covalent bridge may form between two E$^1$ residues; and wherein, X may be an alpha amino isobutyric acid (Aib) or Aib analog. | 39 |
| SEQ. ID. NO. 35 | anti-Her2 two helix binder: VENKCNKEMRNRYWEAALDPNLNNQQ KRXKIRSIYDDPC; wherein, X may be an alpha amino isobutyric acid (Aib) or Aib analog; and the underlined residues on 12, 16, 19, 30, and 34 positions may be substituted with natural amino acids. | 39 |
| SEQ. ID. NO. 36 | anti-Her2 two helix binder: VENKC$^2$NKEMRNRYWEAALDPNLNNQ QKRXKIRSIYDDPC$^2$ wherein X may be an alpha amino isobutyric acid (Aib) or Aib analog; wherein, the residues on 12, 16, 19, 30 and 34 positions may be substituted with natural amino acids (underlined) and C$^2$ may be extended cysteine (e.g., homocysteine). | 39 |
| SEQ. ID. NO. 37 | anti-EGFR two helix binder: VENKC$^2$NKEMWARWEEARNDPNLNGW QMTAKIASIVDDPC$^2$; wherein residues 12, 16, 19, 30 and 34 positions may be substituted with natural amino acids and C$^2$ may be extended cysteine (e.g., homocysteine). | 39 |

TABLE 2-continued

| | | Residues |
|---|---|---|
| SEQ. ID. NO. 38 | anti-EGFR two helix binder: VENKC$^2$NKEFWWRSDEARNDPNLNGW QMTAKIASIADDPC$^2$; wherein, the residues on 12, 16, 19, 30 and 34 positions may have preferred substitutions by natural amino acids (underlined) and C$^2$ may be extended cysteine (e.g., homocysteine). | 39 |
| SEQ. ID. NO. 39 | anti-EGFR two helix binder: C$^2$NKEMWARWEEARNDPNLNGWQMTA KIASIVDDPC$^2$; wherein, the residues on 8, 12, 15, 26 and 30 positions may have preferred substitutions by natural amino acids (underlined) and C$^2$ may be extended cysteine (e.g., homocysteine). | 35 |
| SEQ. ID. NO. 40 | anti-EGFR two helix binder: C$^2$NKEFWWRSDEARNDPNLNGWQMTA KIASIADDPC$^2$; wherein residues 8, 12, 15, 26 and 30 positions may be substituted with natural amino acids, C$^2$ may be extended cysteine (e.g., homocysteine). | 37 |

EXAMPLES

Practice of the invention will be still more fully understood from the following examples, which are presented herein for illustration only and should not be construed as limiting the invention in any way.

Stabilization of two helix polypeptide that bind to human epidermal growth factor receptor type 2 (HER2) may be achieved using different modifications like, introduction of a covalent bridge formed between two allyl-containing side chain amino acids placed in (i–i+7) along the scaffold; addition of novel engineered disulfide bridge formed between cysteines and/or unnatural cysteine analogues and inclusion of natural and unnatural amino acid mutations.

Example 1

Peptide Synthesis & Purification

Selection and determination of two helix polypeptides with binding interface amino acids that bind to a particular target may be accomplished using art recognized display and selection methods such as phage display, ribosomal display, mRNA display yeast surface display, or bacterial surface display techniques. Alternatively, the two helix polypeptides may be designed and synthesized using art recognized techniques as detailed below.

Materials: All N-Fmoc (Fluorenylmethoxycarbonyl)-protected amino acids were purchased from Advanced Chemtech (Louisville, Ky.) except for Fmoc-Cysteine-Acetamidomethyl(Acm)-OH, which was from Novabiochem (San Diego, Calif.). DMF was from Fisher Scientific (Fair Lawn, N.J.). 20% piperidine in DMF and N-methylmorpholine (NMM) in DMF were from Protein Technologies Inc. (Tucson, Ariz.). Trifluoroacetic acid (TFA) and O-(7-azabenzotriazol-1-yl)-N,N,N',N'-trimethyluronium hexafluorophosphate (HATU) was from Advanced Chemtech. Pyridine, acetic anhydride, and anhydrous ether were obtained from J. T. Baker (Phillipsburg, N.J.). Triisopropylsilane (TIS) was purchased from Aldrich Chemical Company (Milwaukee, Wis.). HPLC grade acetonitrile (CH$_3$CN) and Millipore 18 mΩ water were used for peptide purifications.

Stabilization of two helix polypeptides with binding interface amino acids that bind to a particular target may be accomplished using a covalent bridge of 'staple' formed between two allyl amino acids placed in (i–i+7) along the scaffold. Allyl and o-allyl amino acid residues may be introduced in different cases and ring-closing metathesis (RCM) may perform using Grubbs 2nd Generation catalyst to form a staple. Then the peptide may purify by consecutive steps of resin cleavage and iodine oxidation followed by HPLC chromatographic separation. The two helix polypeptides may be designed and synthesized using art recognized techniques as detailed below.

Stabilization of two helix polypeptides with binding interface amino acids that bind to a particular target may be accomplished using novel engineered disulfide bridges formed between cysteines and/or unnatural cysteine analogues. L-cysteine or extended cysteine or hindered cysteine may be introduced in different cases and disulphide bridged scaffold may synthesize and purify by consecutive steps of resin cleavage and iodine oxidation followed by HPLC chromatographic separation. The two helix polypeptides may be designed and synthesized using art recognized techniques as detailed below.

Peptides were synthesized using standard solid phase techniques with N-Fmoc-protected amino acids using 0.2 mmol/g substitution 2,4-dimethoxybenzhydrylamine resin (Rink Resin L S, Advanced Chemtech) on a 50 µM scale. The peptides were synthesized using a Rainin/Protein Technology, Inc. Symphony solid phase peptide synthesizer (Woburn, Mass.).

Prior to any chemistry, the resin was swelled for one hour in Methylene Chloride, subsequently the solvent was exchanged by washing with dimethylformamide (DMF). Each coupling reaction was carried out at room temperature in DMF with five equivalents of amino acid. Reaction times were typically 30 minutes; however residues that were expected to be difficult to couple (for example, bulky trityl-protected residues in the latter half of synthesis were either coupled for 45 minutes or double coupled (20 minutes×2). The coupling reagent used was HATU with NMM as the base. For each step the coupling agent was delivered at a scale of five equivalents relative to the estimated resin capacity, and reaction carried out in 5.0 ml of 0.05 M amino acid reagent, 0.05 M HATU, 0.2 M NMM solution in DMF.

The reactions did not perturb the side-chains of the amino acids, which were typically protected with acid labile groups if reactive groups were present. Generally, the tyrosine, threonine, serine, and aspartic acid side chains were protected as the corresponding tert-butyl esters. The lysine side chains were t-Butoxycarbonyl (Boc) protected. The glutamine side chain was protected as the N-γ-trityl derivative, and the arginine side chain was protected as the 2,2,5,7,8-Pentamethyl-chromane-6-sulfonyl derivative. The cysteine amino acid side chain thiol group was protected with Acm.

Following each coupling reaction, the N-terminal Fmoc-protected amine was deprotected by applying 20% piperidine in DMF twice at room temperature for approximately 15 minutes. After the addition of the last residue the resin, still on the peptide synthesizer, was rinsed thoroughly with DMF and methylene chloride before being dried under a stream of nitrogen for 20 minutes.

To cleave the peptides from the resin a cocktail consisting of 10 mL 95% TFA, 2.5% TIS and 2.5% water was used. The resin and cocktail were stirred at room temperature for approximately 4 hours. This cocktail did not remove the Acm protecting group on the cysteine thiols. The resin beads were removed by filtering through a polyethylene disc with 30 um pore size. The peptide was precipitated with 40 ml of ice-cold ether and centrifuged at 3000 r.c.f. until the precipitate formed a pellet at the bottom of the centrifuge tube. The ether was decanted, and the pellet was resuspended in cold ether and centrifuged again; this process was repeated two times. Between 10 ml and 40 ml of water was added to the decanted pellet to solubilize the peptide and the resulting solution was lyophilized.

Peptides were purified by reverse phase preparative HPLC with a C4-silica column (Vydac, Hesperia, Calif.). The peptide chromatograms can be monitored at 220 nm, which corresponds to the absorption of the amide chromophore. A solvent system including $CH_3CN$/TFA (acetonitrile/Trifluoroacetic acid; 100:0.05) and $H_2O$/TFA (water/Trifluoroacetic acid; 100:0.05) eluents at flow rates of 25 ml/min preparative runs. Dissolved crude peptides in Millipore water can be injected at a scale of 1.5 mg and 5-10 mg peptide for semi-preparative or preparative, respectively. The chromatogram shape was analyzed to ensure good resolution and peak shape. Gradient conditions for all peptides were typically 0.5% of $CH_3CN$/TFA (100:0.01) per minute. Target peptide identity was confirmed by matrix-assisted laser desorption time-of-flight mass spectroscopy (MALDI) or electrospray ionization mass spectrometry (ESI).

After initial purification, the Acm-protecting group was removed from the peptide using a one step deprotection/oxidization reaction in the presence of iodine. This step was carried out using concentrations favorable to intramolecular disulfide formation (0.1 mg/ml). Peptide was dissolve in 1:1 water:Acetic acid at ~1 mg/ml or less. Nine volumes of 1 M HCl were then added followed by 10 equivalents $I_2$/Acm of a 0.1 M $I_2$ solution. This solution was vigorously stirred for 30 minutes at room temperature and the reaction was quenched by the dropwise addition of 1 M sodium thiosulfate until the solution became clear. This resulting product was then purified using the same reverse phase HPLC gradient as the initial purification. The desired fractions were frozen immediately and lyophilized. Target peptide identity was confirmed by MALDI or ESI.

To make 'covalent bridge of staple', two allyl amino acids placed in (i–i+7) positions were subjected to ring closing metathesis using Hoveyda-Grubbs 2nd generation catalyst to form a staple. The ring closing metathesis was carried out with the peptide still bound to the resin beads. A 50 µL of a degassed 10 mM solution of Hoveyda-Grubbs Catalyst Generation 2 in 1,2-dichloroethane was added to a suspension of 50 mg resin in 250 µL of 1,2-dichloroethane. The reaction was allowed to process at 60° C. for 18 hours and the catalyst was filtered off. The addition of catalyst and metathesis reaction for 18 hour was repeated once. The resin beads were washed with dichloromethane and dried. This resulting product was then cleaved from the resin and purified with reverse phase HPLC using the same protocol described above. The desired fractions were frozen immediately and lyophilized. Target peptide identity was confirmed by MALDI or ESI.

After initial purification of the peptide for engineered disulfide linkage, the Acm-protecting group was removed from the peptide using a one step deprotection/oxidization reaction in the presence of iodine. This step was carried out using concentrations favorable to intramolecular disulfide formation (0.1 mg/ml). Peptide was dissolve in 1:1 water:Acetic acid at ~1 mg/ml or less. Nine volumes of 1 M HCl were then added followed by 10 equivalents $I_2$/Acm of a 0.1 M $I_2$ solution. This solution was vigorously stirred for 30 minutes at room temperature and the reaction was quenched by the dropwise addition of 1M sodium thiosulfate until the solution became clear. This resulting product was then purified using the same reverse phase HPLC gradient as the initial purification. The desired fractions were frozen immediately and lyophilized. Target peptide identity was confirmed by MALDI or ESI.

Example 2

Target Binding Analysis

Binding interactions between the binder and the Her2/neu antigen was measured in vitro using surface plasmon resonance (SPR) detection on a BIAcore™ 3000 instrument (Piscataway, N.J.). The extracellular domain of the Her2/neu antigen was obtained as a conjugate with the Fc region of human IgG (Fc-Her2) from R&D Systems and covalently attached to a CM-5 dextran-functionalized sensor chip (BIAcore™) pre-equilibrated with HBS-EP buffer (0.00M HEPES pH 7.4, 0.15M NaCl, 3 mM EDTA, 0.005% v/v surfactant P20) at 10 µL/min and subsequently activated with 1-ethyl-3-[3-dimethylaminopropyl]carbodiimide hydrochloride (EDC) and N-hydroxysuccinimide (NHS). The Fc-Her2 (5 µg/ml) in 10 mM sodium acetate (pH 5.5) was injected onto the activated sensor chip until the desired immobilization level was achieved (2 min). Residual activated groups on the sensor chip were blocked by injection of ethanolamine (1 M, pH 8.5). Any non-covalently bound conjugate was removed by repeated (n=5) washing with 2.5 M $NaCl_2$, 50 mM NaOH.

A second flow cell on the same sensor chip was treated identically, except with no Fc-Her2 immobilization, to serve as a control surface for refractive index changes and non-specific binding interactions with the sensor chip. Prior to the kinetic study, binding of the target analyte was tested on both surfaces and a surface stability experiment was performed to ensure adequate removal of the bound analyte and regeneration of the sensor chip following treatment with 2.5 M NaCl, 50 mM NaOH. SPR sensorgrams were analyzed using the BiaEval (BIAcore) software. The robustness of the kinetic model was determined by evaluation of the residuals and standard error for each of the calculated kinetic parameters, the "goodness of the fit" ($\chi^2$<10), and a direct comparison of the modeled sensorgrams to the experimental data.

The binding interactions between the generated peptide and Fc-Her2 conjugate were measured using SPR (BIAcore). To minimize mass transport limitations, a surface density of ~3000 Rus (Response Units) Fc-Her2 was used, resulting in a maximal binding response ~100 RU with ~100 nM of the synthesized peptide. SPR measurements were collected at eight analyte concentrations (0-100 nM peptide) and the resulting sensorgrams were fitted to a 1:1 Langmuir binding model.

For analysis of the IgG binding peptide, the same protocol was followed as above except that human IgG was immobilized by injecting 20 µg/ml in 10 mM sodium acetate (pH 5.0) onto the activated sensor chip until the desired immobilization level was achieved (2 minutes).

Example 3

CD Spectroscopy

Secondary structure of different 2-helix scaffold was determined by CD analysis. All CD spectra were obtained on an JASCO J-815 CD spectropolarimeter in the wavelength range of 250-185 nm using 1 nm bandwidth, 0.5 nm resolution, 4 seconds averaging time, 3 scan per sample, 0 second delay, and a path length of 1 mm. Spectra were recorded at 20° C., unless otherwise noted, in a thermostated circular cuvette, with peptide concentrations of 15 μM in 13 mM of $K_2HPO4$ buffer at pH8. Results are reported as mean residue ellipticity (MRW).

The analysis of CD data shows that % helicity of 2-Helix binder with S—S bridge (this one does not have 5 scaffold substitutions) formed between L-cysteines is 11. The 2-helix binder with 5 scaffold substitutions and without S—S is 8 whereas the same for 2-Helix scaffold containing S—S formed between extended cysteine is 15. So, the secondary structure of different 2-helix scaffolds is comparable from CD spectroscopy.

EQUIVALENTS

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein.

The invention claimed is:

1. An isolated polypeptide selected from the group consisting of:

VENKC²NKE¹MRNRYWE¹AALDPNLNNQQKRXKI RSIYDDPC²(SEQ ID NO. 32) or a four-residue N-terminal truncated variant of SEQ ID NO. 32, wherein $E^1$ is selected from an O-allyl glutamic acid or an O-allyl glutamic acid analog, and a covalent bridge is between two $E^1$ residues, wherein, X is alpha amino isobutyric acid or an alpha amino isobutyric acid analog other than a naturally occurring amino acid; $C^2$ is an extended cysteine, wherein a disulfide bond connects the $C^2$ residues; and wherein the polypeptide binds specifically to human epidermal growth factor receptor 2 (Her2).

2. The polypeptide of claim 1, further comprising a signal generator, that is attached to the polypeptide, and that is selected from a fluorescent probe, a radioactive probe, or a paramagnetic probe.

3. The polypeptide of claim 2, wherein the signal generator comprises a pH-sensitive cyanine dye.

4. The polypeptide of claim 2, wherein the signal generator comprises $^{11}C$, $^{18}F$, $^{32}P$ or $^{99m}Tc$.

5. The polypeptide of claim 2, wherein the signal generator comprises a paramagnetic probe.

6. A method of identifying Her2 in a sample comprising:
   (a) contacting the polypeptide of claim 2 with the sample, and
   (b) observing a signal produced by the signal generator selected from a fluorescence probe, a radioactive probe, or a paramagnetic probe.

7. The method of claim 6, further comprising quantifying the amount of Her2 present in the sample.

* * * * *

```
                         SEQUENCE LISTING

<160> NUMBER OF SEQ ID NOS: 44

<210> SEQ ID NO 1
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 2
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(7)
<223> OTHER INFORMATION: Any of the twenty naturally occurring amino
      acids
<220> FEATURE:
<221> NAME/KEY: MOD_RES
<222> LOCATION: (9)..(10)
<223> OTHER INFORMATION: Any of the twenty naturally occurring amino
      acids
<220> FEATURE:
<221> NAME/KEY: MOD_RES
<222> LOCATION: (13)..(14)
<223> OTHER INFORMATION: Any of the twenty naturally occurring amino
      acids
<220> FEATURE:
<221> NAME/KEY: MOD_RES
<222> LOCATION: (20)..(21)
<223> OTHER INFORMATION: Any of the twenty naturally occurring amino
      acids
<220> FEATURE:
<221> NAME/KEY: MOD_RES
<222> LOCATION: (23)..(24)
```

```
<223> OTHER INFORMATION: Any of the twenty naturally occurring amino
      acids
<220> FEATURE:
<221> NAME/KEY: MOD_RES
<222> LOCATION: (28)..(28)
<223> OTHER INFORMATION: Any of the twenty naturally occurring amino
      acids
<220> FEATURE:
<221> NAME/KEY: MOD_RES
<222> LOCATION: (31)..(31)
<223> OTHER INFORMATION: Any of the twenty naturally occurring amino
      acids

<400> SEQUENCE: 2

Phe Asn Lys Glu Xaa Xaa Xaa Ala Xaa Xaa Glu Ile Xaa Xaa Leu Pro
1               5                   10                  15

Asn Leu Asn Xaa Xaa Gln Xaa Xaa Ala Phe Ile Xaa Ser Leu Xaa Asp
            20                  25                  30

Asp Pro Ser
        35

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asp or Glu

<400> SEQUENCE: 3

Val Xaa Asn Lys
1

<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Asp or Glu
<220> FEATURE:
<221> NAME/KEY: MOD_RES
<222> LOCATION: (9)..(11)
<223> OTHER INFORMATION: Any of the twenty naturally occurring amino
      acids
<220> FEATURE:
<221> NAME/KEY: MOD_RES
<222> LOCATION: (13)..(14)
<223> OTHER INFORMATION: Any of the twenty naturally occurring amino
      acids
<220> FEATURE:
<221> NAME/KEY: MOD_RES
<222> LOCATION: (17)..(18)
<223> OTHER INFORMATION: Any of the twenty naturally occurring amino
      acids
<220> FEATURE:
<221> NAME/KEY: MOD_RES
<222> LOCATION: (24)..(25)
<223> OTHER INFORMATION: Any of the twenty naturally occurring amino
      acids
<220> FEATURE:
<221> NAME/KEY: MOD_RES
<222> LOCATION: (27)..(28)
<223> OTHER INFORMATION: Any of the twenty naturally occurring amino
      acids
<220> FEATURE:
```

```
<221> NAME/KEY: MOD_RES
<222> LOCATION: (32)..(32)
<223> OTHER INFORMATION: Any of the twenty naturally occurring amino
      acids
<220> FEATURE:
<221> NAME/KEY: MOD_RES
<222> LOCATION: (35)..(35)
<223> OTHER INFORMATION: Any of the twenty naturally occurring amino
      acids

<400> SEQUENCE: 4

Val Xaa Asn Lys Phe Asn Lys Glu Xaa Xaa Xaa Ala Xaa Xaa Glu Ile
1               5                   10                  15

Xaa Xaa Leu Pro Asn Leu Asn Xaa Xaa Gln Xaa Xaa Ala Phe Ile Xaa
            20                  25                  30

Ser Leu Xaa Asp Asp Pro Ser
            35

<210> SEQ ID NO 5
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Asp or Glu

<400> SEQUENCE: 5

Val Xaa Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser
            35

<210> SEQ ID NO 6
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Asp or Glu

<400> SEQUENCE: 6

Val Xaa Asn Lys Phe Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Ser
            35

<210> SEQ ID NO 7
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7
```

-continued

Val Glu Asn Lys Cys Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Cys
            35

<210> SEQ ID NO 8
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Val Glu Asn Lys Cys Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Cys
            35

<210> SEQ ID NO 9
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Val Glu Asn Lys Phe Cys Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Cys
            35

<210> SEQ ID NO 10
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Val Glu Asn Cys Phe Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Cys
            35

<210> SEQ ID NO 11
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

-continued

```
Val Glu Asn Lys Phe Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Gly
        35
```

<210> SEQ ID NO 12
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: O-allyl glutamic acid or analog thereof
<220> FEATURE:
<221> NAME/KEY: MOD_RES
<222> LOCATION: (15)..(15)
<223> OTHER INFORMATION: O-allyl glutamic acid or analog thereof

<400> SEQUENCE: 12

```
Val Glu Asn Lys Cys Asn Lys Xaa Met Arg Asn Ala Tyr Trp Xaa Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Cys
        35
```

<210> SEQ ID NO 13
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: O-allyl glutamic acid or analog thereof
<220> FEATURE:
<221> NAME/KEY: MOD_RES
<222> LOCATION: (15)..(15)
<223> OTHER INFORMATION: O-allyl aspartic acid or analog thereof

<400> SEQUENCE: 13

```
Val Glu Asn Lys Cys Asn Lys Xaa Met Arg Asn Ala Tyr Trp Xaa Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Cys
        35
```

<210> SEQ ID NO 14
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: (2S)-Fmoc-2-amino-8-nonenoic acid or analog
      thereof
<220> FEATURE:
<221> NAME/KEY: MOD_RES

```
<222> LOCATION: (15)..(15)
<223> OTHER INFORMATION: (2S)-Fmoc-2-amino-8-nonenoic acid or analog
      thereof

<400> SEQUENCE: 14

Val Glu Asn Lys Cys Asn Lys Xaa Met Arg Asn Ala Tyr Trp Xaa Ile
1               5                   10                  15

Ala Leu Leu Pro Asn Leu Asn Asn Gln Gln Lys Arg Ala Phe Ile Arg
            20                  25                  30

Ser Leu Tyr Asp Pro Cys
        35

<210> SEQ ID NO 15
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: O-allyl glutamic acid or analog thereof
<220> FEATURE:
<221> NAME/KEY: MOD_RES
<222> LOCATION: (33)..(33)
<223> OTHER INFORMATION: O-allyl glutamic acid or analog thereof

<400> SEQUENCE: 15

Val Glu Asn Lys Cys Asn Lys Glu Met Arg Asn Ala Tyr Trp Glu Ile
1               5                   10                  15

Ala Leu Leu Pro Asn Leu Asn Asn Gln Xaa Lys Arg Ala Phe Ile Arg
            20                  25                  30

Xaa Leu Tyr Asp Asp Pro Cys
        35

<210> SEQ ID NO 16
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: O-allyl glutamic acid or analog thereof
<220> FEATURE:
<221> NAME/KEY: MOD_RES
<222> LOCATION: (33)..(33)
<223> OTHER INFORMATION: O-allyl aspartic acid or analog thereof

<400> SEQUENCE: 16

Val Glu Asn Lys Cys Asn Lys Glu Met Arg Asn Ala Tyr Trp Glu Ile
1               5                   10                  15

Ala Leu Leu Pro Asn Leu Asn Asn Gln Xaa Lys Arg Ala Phe Ile Arg
            20                  25                  30

Xaa Leu Tyr Asp Asp Pro Cys
        35

<210> SEQ ID NO 17
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (26)..(26)
<223> OTHER INFORMATION: (2S)-Fmoc-2-amino-8-nonenoic acid or analog
      thereof
<220> FEATURE:
<221> NAME/KEY: MOD_RES
<222> LOCATION: (33)..(33)
<223> OTHER INFORMATION: (2S)-Fmoc-2-amino-8-nonenoic acid or analog
      thereof

<400> SEQUENCE: 17

Val Glu Asn Lys Cys Asn Lys Glu Met Arg Asn Ala Tyr Trp Glu Ile
1               5                   10                  15

Ala Leu Leu Pro Asn Leu Asn Asn Gln Xaa Lys Arg Ala Phe Ile Arg
            20                  25                  30

Xaa Leu Tyr Asp Asp Pro Cys
        35

<210> SEQ ID NO 18
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Cys or analog thereof
<220> FEATURE:
<221> NAME/KEY: MOD_RES
<222> LOCATION: (39)..(39)
<223> OTHER INFORMATION: Cys or analog thereof

<400> SEQUENCE: 18

Val Glu Asn Lys Xaa Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Xaa
        35

<210> SEQ ID NO 19
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Cysteine derivative with two methyl groups
      attached to the Beta-carbon of the side-chain

<400> SEQUENCE: 19

Val Glu Asn Lys Xaa Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Cys
        35

<210> SEQ ID NO 20
<211> LENGTH: 39
<212> TYPE: PRT
<213> ORGANISM: Artificial Sequence
<220> FEATURE:
```

-continued

```
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: An unnatural amino acid derivative analogous to
      the naturally occurring cysteine but with an extra
      methyl group in the side-chain

<400> SEQUENCE: 20

Val Glu Asn Lys Xaa Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Cys
        35

<210> SEQ ID NO 21
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: An unnatural amino acid derivative analogous to
      the naturally occurring cysteine but with an extra
      methyl group in the side-chain
<220> FEATURE:
<221> NAME/KEY: MOD_RES
<222> LOCATION: (39)..(39)
<223> OTHER INFORMATION: An unnatural amino acid derivative analogous to
      the naturally occurring cysteine but with an extra
      methyl group in the side-chain

<400> SEQUENCE: 21

Val Glu Asn Lys Xaa Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Xaa
        35

<210> SEQ ID NO 22
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Cysteine derivative with two methyl groups
      attached to the Beta-carbon of the side-chain
<220> FEATURE:
<221> NAME/KEY: MOD_RES
<222> LOCATION: (39)..(39)
<223> OTHER INFORMATION: An unnatural amino acid derivative analogous to
      the naturally occurring cysteine but with an extra
      methyl group in the side-chain

<400> SEQUENCE: 22

Val Glu Asn Lys Xaa Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30
```

Ser Leu Tyr Asp Asp Pro Xaa
        35

<210> SEQ ID NO 23
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (39)..(39)
<223> OTHER INFORMATION: Cysteine derivative with two methyl groups
      attached to the Beta-carbon of the side-chain

<400> SEQUENCE: 23

Val Glu Asn Lys Cys Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Xaa
        35

<210> SEQ ID NO 24
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Alpha amino isobutyric acid or analog thereof
<220> FEATURE:
<221> NAME/KEY: MOD_RES
<222> LOCATION: (12)..(12)
<223> OTHER INFORMATION: Alpha amino isobutyric acid or analog thereof
<220> FEATURE:
<221> NAME/KEY: MOD_RES
<222> LOCATION: (16)..(16)
<223> OTHER INFORMATION: Alpha amino isobutyric acid or analog thereof

<400> SEQUENCE: 24

Val Glu Asn Lys Cys Asn Lys Xaa Met Arg Asn Xaa Tyr Trp Glu Xaa
1               5                   10                  15

Ala Leu Leu Pro Asn Leu Asn Asn Gln Gln Lys Arg Ala Phe Ile Arg
            20                  25                  30

Ser Leu Tyr Asp Asp Pro Cys
        35

<210> SEQ ID NO 25
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: Alpha amino isobutyric acid or analog thereof
<220> FEATURE:
<221> NAME/KEY: MOD_RES
<222> LOCATION: (30)..(30)
<223> OTHER INFORMATION: Alpha amino isobutyric acid or analog thereof
<220> FEATURE:
<221> NAME/KEY: MOD_RES
<222> LOCATION: (34)..(34)
<223> OTHER INFORMATION: Alpha amino isobutyric acid or analog thereof

```
<400> SEQUENCE: 25

Val Glu Asn Lys Cys Asn Lys Glu Met Arg Asn Ala Tyr Trp Glu Ile
1               5                   10                  15

Ala Leu Leu Pro Asn Leu Asn Asn Gln Xaa Lys Arg Ala Xaa Ile Arg
            20                  25                  30

Ser Xaa Tyr Asp Asp Pro Cys
        35

<210> SEQ ID NO 26
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Alpha amino isobutyric acid or analog thereof
<220> FEATURE:
<221> NAME/KEY: MOD_RES
<222> LOCATION: (12)..(12)
<223> OTHER INFORMATION: Alpha amino isobutyric acid or analog thereof
<220> FEATURE:
<221> NAME/KEY: MOD_RES
<222> LOCATION: (16)..(16)
<223> OTHER INFORMATION: Alpha amino isobutyric acid or analog thereof
<220> FEATURE:
<221> NAME/KEY: MOD_RES
<222> LOCATION: (26)..(26)
<223> OTHER INFORMATION: Alpha amino isobutyric acid or analog thereof
<220> FEATURE:
<221> NAME/KEY: MOD_RES
<222> LOCATION: (30)..(30)
<223> OTHER INFORMATION: Alpha amino isobutyric acid or analog thereof
<220> FEATURE:
<221> NAME/KEY: MOD_RES
<222> LOCATION: (34)..(34)
<223> OTHER INFORMATION: Alpha amino isobutyric acid or analog thereof

<400> SEQUENCE: 26

Val Glu Asn Lys Cys Asn Lys Xaa Met Arg Asn Xaa Tyr Trp Glu Xaa
1               5                   10                  15

Ala Leu Leu Pro Asn Leu Asn Asn Gln Xaa Lys Arg Ala Xaa Ile Arg
            20                  25                  30

Ser Xaa Tyr Asp Asp Pro Cys
        35

<210> SEQ ID NO 27
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (29)..(29)
<223> OTHER INFORMATION: Alpha amino isobutyric acid or analog thereof

<400> SEQUENCE: 27

Val Glu Asn Lys Cys Asn Lys Glu Met Arg Asn Ala Tyr Trp Glu Ile
1               5                   10                  15

Ala Leu Leu Pro Asn Leu Asn Asn Gln Gln Lys Arg Xaa Phe Ile Arg
            20                  25                  30

Ser Leu Tyr Asp Asp Pro Cys
        35
```

<210> SEQ ID NO 28
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 28

Val Glu Asn Lys Cys Asn Lys Glu Met Arg Asn Arg Tyr Trp Glu Ala
1               5                   10                  15

Ala Leu Asp Pro Asn Leu Asn Asn Gln Gln Lys Arg Ala Lys Ile Arg
            20                  25                  30

Ser Ile Tyr Asp Asp Pro Cys
        35

<210> SEQ ID NO 29
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: An unnatural amino acid derivative analogous to
      the naturally occurring cysteine but with an extra
      methyl group in the side-chain
<220> FEATURE:
<221> NAME/KEY: MOD_RES
<222> LOCATION: (39)..(39)
<223> OTHER INFORMATION: An unnatural amino acid derivative analogous to
      the naturally occurring cysteine but with an extra
      methyl group in the side-chain
<220> FEATURE:
<223> OTHER INFORMATION: see specification as filed for detailed
      description of substitutions and preferred embodiments

<400> SEQUENCE: 29

Val Glu Asn Lys Xaa Asn Lys Glu Met Arg Asn Arg Tyr Trp Glu Ala
1               5                   10                  15

Ala Leu Asp Pro Asn Leu Asn Asn Gln Gln Lys Arg Ala Lys Ile Arg
            20                  25                  30

Ser Ile Tyr Asp Asp Pro Xaa
        35

<210> SEQ ID NO 30
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: O-allyl glutamic acid or analog thereof
<220> FEATURE:
<221> NAME/KEY: MOD_RES
<222> LOCATION: (15)..(15)
<223> OTHER INFORMATION: O-allyl glutamic acid or analog thereof
<220> FEATURE:
<221> NAME/KEY: MOD_RES
<222> LOCATION: (29)..(29)
<223> OTHER INFORMATION: Alpha amino isobutyric acid or analog thereof

<400> SEQUENCE: 30

-continued

```
Val Glu Asn Lys Cys Asn Lys Xaa Met Arg Asn Ala Tyr Trp Xaa Ile
1               5                   10                  15

Ala Leu Leu Pro Asn Leu Asn Asn Gln Gln Lys Arg Xaa Phe Ile Arg
            20                  25                  30

Ser Leu Tyr Asp Asp Pro Cys
        35

<210> SEQ ID NO 31
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: O-allyl glutamic acid or analog thereof
<220> FEATURE:
<221> NAME/KEY: MOD_RES
<222> LOCATION: (15)..(15)
<223> OTHER INFORMATION: O-allyl glutamic acid or analog thereof
<220> FEATURE:
<221> NAME/KEY: MOD_RES
<222> LOCATION: (29)..(29)
<223> OTHER INFORMATION: Alpha amino isobutyric acid or analog thereof
<220> FEATURE:
<223> OTHER INFORMATION: see specification as filed for detailed
      description of substitutions and preferred embodiments

<400> SEQUENCE: 31

Val Glu Asn Lys Cys Asn Lys Xaa Met Arg Asn Arg Tyr Trp Xaa Ala
1               5                   10                  15

Ala Leu Asp Pro Asn Leu Asn Asn Gln Gln Lys Arg Xaa Lys Ile Arg
            20                  25                  30

Ser Ile Tyr Asp Asp Pro Cys
        35

<210> SEQ ID NO 32
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: An unnatural amino acid derivative analogous to
      the naturally occurring cysteine but with an extra
      methyl group in the side-chain
<220> FEATURE:
<221> NAME/KEY: MOD_RES
<222> LOCATION: (8)..(8)
<223> OTHER INFORMATION: O-allyl glutamic acid or analog thereof
<220> FEATURE:
<221> NAME/KEY: MOD_RES
<222> LOCATION: (15)..(15)
<223> OTHER INFORMATION: O-allyl glutamic acid or analog thereof
<220> FEATURE:
<221> NAME/KEY: MOD_RES
<222> LOCATION: (29)..(29)
<223> OTHER INFORMATION: Alpha amino isobutyric acid or analog thereof
<220> FEATURE:
<221> NAME/KEY: MOD_RES
<222> LOCATION: (39)..(39)
<223> OTHER INFORMATION: An unnatural amino acid derivative analogous to
      the naturally occurring cysteine but with an extra
      methyl group in the side-chain
<220> FEATURE:
<223> OTHER INFORMATION: see specification as filed for detailed
      description of substitutions and preferred embodiments
```

```
<400> SEQUENCE: 32

Val Glu Asn Lys Xaa Asn Lys Xaa Met Arg Asn Arg Tyr Trp Xaa Ala
1               5                   10                  15

Ala Leu Asp Pro Asn Leu Asn Asn Gln Gln Lys Arg Xaa Lys Ile Arg
            20                  25                  30

Ser Ile Tyr Asp Asp Pro Xaa
            35

<210> SEQ ID NO 33
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: An unnatural amino acid derivative analogous to
      the naturally occurring cysteine but with an extra
      methyl group in the side-chain
<220> FEATURE:
<221> NAME/KEY: MOD_RES
<222> LOCATION: (29)..(29)
<223> OTHER INFORMATION: Alpha amino isobutyric acid or analog thereof
<220> FEATURE:
<221> NAME/KEY: MOD_RES
<222> LOCATION: (39)..(39)
<223> OTHER INFORMATION: An unnatural amino acid derivative analogous to
      the naturally occurring cysteine but with an extra
      methyl group in the side-chain

<400> SEQUENCE: 33

Val Glu Asn Lys Xaa Asn Lys Glu Met Arg Asn Ala Tyr Trp Glu Ile
1               5                   10                  15

Ala Leu Leu Pro Asn Leu Asn Asn Gln Gln Lys Arg Xaa Phe Ile Arg
            20                  25                  30

Ser Leu Tyr Asp Asp Pro Xaa
            35

<210> SEQ ID NO 34
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: An unnatural amino acid derivative analogous to
      the naturally occurring cysteine but with an extra
      methyl group in the side-chain
<220> FEATURE:
<221> NAME/KEY: MOD_RES
<222> LOCATION: (8)..(8)
<223> OTHER INFORMATION: O-allyl glutamic acid or analog thereof
<220> FEATURE:
<221> NAME/KEY: MOD_RES
<222> LOCATION: (15)..(15)
<223> OTHER INFORMATION: O-allyl glutamic acid or analog thereof
<220> FEATURE:
<221> NAME/KEY: MOD_RES
<222> LOCATION: (29)..(29)
<223> OTHER INFORMATION: Alpha amino isobutyric acid or analog thereof
<220> FEATURE:
<221> NAME/KEY: MOD_RES
<222> LOCATION: (39)..(39)
<223> OTHER INFORMATION: An unnatural amino acid derivative analogous to
      the naturally occurring cysteine but with an extra
      methyl group in the side-chain
```

```
<400> SEQUENCE: 34

Val Glu Asn Lys Xaa Asn Lys Xaa Met Arg Asn Ala Tyr Trp Xaa Ile
1               5                   10                  15

Ala Leu Leu Pro Asn Leu Asn Asn Gln Gln Lys Arg Xaa Phe Ile Arg
            20                  25                  30

Ser Leu Tyr Asp Asp Pro Xaa
        35

<210> SEQ ID NO 35
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (29)..(29)
<223> OTHER INFORMATION: Alpha amino isobutyric acid or analog thereof
<220> FEATURE:
<223> OTHER INFORMATION: see specification as filed for detailed
      description of substitutions and preferred embodiments

<400> SEQUENCE: 35

Val Glu Asn Lys Cys Asn Lys Glu Met Arg Asn Arg Tyr Trp Glu Ala
1               5                   10                  15

Ala Leu Asp Pro Asn Leu Asn Asn Gln Gln Lys Arg Xaa Lys Ile Arg
            20                  25                  30

Ser Ile Tyr Asp Asp Pro Cys
        35

<210> SEQ ID NO 36
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: An unnatural amino acid derivative analogous to
      the naturally occurring cysteine but with an extra
      methyl group in the side-chain
<220> FEATURE:
<221> NAME/KEY: MOD_RES
<222> LOCATION: (29)..(29)
<223> OTHER INFORMATION: Alpha amino isobutyric acid or analog thereof
<220> FEATURE:
<221> NAME/KEY: MOD_RES
<222> LOCATION: (39)..(39)
<223> OTHER INFORMATION: An unnatural amino acid derivative analogous to
      the naturally occurring cysteine but with an extra
      methyl group in the side-chain
<220> FEATURE:
<223> OTHER INFORMATION: see specification as filed for detailed
      description of substitutions and preferred embodiments

<400> SEQUENCE: 36

Val Glu Asn Lys Xaa Asn Lys Glu Met Arg Asn Arg Tyr Trp Glu Ala
1               5                   10                  15

Ala Leu Asp Pro Asn Leu Asn Asn Gln Gln Lys Arg Xaa Lys Ile Arg
            20                  25                  30

Ser Ile Tyr Asp Asp Pro Xaa
        35

<210> SEQ ID NO 37
```

```
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: An unnatural amino acid derivative analogous to
      the naturally occurring cysteine but with an extra
      methyl group in the side-chain
<220> FEATURE:
<221> NAME/KEY: MOD_RES
<222> LOCATION: (39)..(39)
<223> OTHER INFORMATION: An unnatural amino acid derivative analogous to
      the naturally occurring cysteine but with an extra
      methyl group in the side-chain
<220> FEATURE:
<223> OTHER INFORMATION: see specification as filed for detailed
      description of substitutions and preferred embodiments

<400> SEQUENCE: 37

Val Glu Asn Lys Xaa Asn Lys Glu Met Trp Ala Arg Trp Glu Ala
1               5                   10                  15

Arg Asn Asp Pro Asn Leu Asn Gly Trp Gln Met Thr Ala Lys Ile Ala
            20                  25                  30

Ser Ile Val Asp Asp Pro Xaa
        35

<210> SEQ ID NO 38
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: An unnatural amino acid derivative analogous to
      the naturally occurring cysteine but with an extra
      methyl group in the side-chain
<220> FEATURE:
<221> NAME/KEY: MOD_RES
<222> LOCATION: (39)..(39)
<223> OTHER INFORMATION: An unnatural amino acid derivative analogous to
      the naturally occurring cysteine but with an extra
      methyl group in the side-chain
<220> FEATURE:
<223> OTHER INFORMATION: see specification as filed for detailed
      description of substitutions and preferred embodiments

<400> SEQUENCE: 38

Val Glu Asn Lys Xaa Asn Lys Glu Phe Trp Trp Arg Ser Asp Glu Ala
1               5                   10                  15

Arg Asn Asp Pro Asn Leu Asn Gly Trp Gln Met Thr Ala Lys Ile Ala
            20                  25                  30

Ser Ile Ala Asp Asp Pro Xaa
        35

<210> SEQ ID NO 39
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: An unnatural amino acid derivative analogous to
```

```
      the naturally occurring cysteine but with an extra
      methyl group in the side-chain
<220> FEATURE:
<221> NAME/KEY: MOD_RES
<222> LOCATION: (35)..(35)
<223> OTHER INFORMATION: An unnatural amino acid derivative analogous to
      the naturally occurring cysteine but with an extra
      methyl group in the side-chain
<220> FEATURE:
<223> OTHER INFORMATION: see specification as filed for detailed
      description of substitutions and preferred embodiments

<400> SEQUENCE: 39

Xaa Asn Lys Glu Met Trp Ala Arg Trp Glu Glu Ala Arg Asn Asp Pro
1               5                   10                  15

Asn Leu Asn Gly Trp Gln Met Thr Ala Lys Ile Ala Ser Ile Val Asp
            20                  25                  30

Asp Pro Xaa
        35

<210> SEQ ID NO 40
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: An unnatural amino acid derivative analogous to
      the naturally occurring cysteine but with an extra
      methyl group in the side-chain
<220> FEATURE:
<221> NAME/KEY: MOD_RES
<222> LOCATION: (35)..(35)
<223> OTHER INFORMATION: An unnatural amino acid derivative analogous to
      the naturally occurring cysteine but with an extra
      methyl group in the side-chain
<220> FEATURE:
<223> OTHER INFORMATION: see specification as filed for detailed
      description of substitutions and preferred embodiments

<400> SEQUENCE: 40

Xaa Asn Lys Glu Phe Trp Trp Arg Ser Asp Glu Ala Arg Asn Asp Pro
1               5                   10                  15

Asn Leu Asn Gly Trp Gln Met Thr Ala Lys Ile Ala Ser Ile Ala Asp
            20                  25                  30

Asp Pro Xaa
        35

<210> SEQ ID NO 41
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Cys or analog thereof
<220> FEATURE:
<221> NAME/KEY: MOD_RES
<222> LOCATION: (39)..(39)
<223> OTHER INFORMATION: Cys or analog thereof

<400> SEQUENCE: 41

Val Glu Asn Lys Xaa Asn Lys Glu Met Arg Asn Arg Tyr Trp Glu Ala
1               5                   10                  15
```

-continued

Ala Leu Asp Pro Asn Leu Asn Asn Gln Gln Lys Arg Ala Lys Ile Arg
            20                  25                  30

Ser Ile Tyr Asp Asp Pro Xaa
        35

<210> SEQ ID NO 42
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: O-allyl glutamic acid or analog thereof
<220> FEATURE:
<221> NAME/KEY: MOD_RES
<222> LOCATION: (11)..(11)
<223> OTHER INFORMATION: O-allyl glutamic acid or analog thereof
<220> FEATURE:
<221> NAME/KEY: MOD_RES
<222> LOCATION: (25)..(25)
<223> OTHER INFORMATION: Alpha amino isobutyric acid or analog thereof

<400> SEQUENCE: 42

Cys Asn Lys Xaa Met Arg Asn Ala Tyr Trp Xaa Ile Ala Leu Leu Pro
1               5                   10                  15

Asn Leu Asn Asn Gln Gln Lys Arg Xaa Phe Ile Arg Ser Leu Tyr Asp
            20                  25                  30

Asp Pro Cys
        35

<210> SEQ ID NO 43
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: An unnatural amino acid derivative analogous to
      the naturally occurring cysteine but with an extra
      methyl group in the side-chain
<220> FEATURE:
<221> NAME/KEY: MOD_RES
<222> LOCATION: (8)..(8)
<223> OTHER INFORMATION: O-allyl glutamic acid
<220> FEATURE:
<221> NAME/KEY: MOD_RES
<222> LOCATION: (15)..(15)
<223> OTHER INFORMATION: O-allyl glutamic acid
<220> FEATURE:
<221> NAME/KEY: MOD_RES
<222> LOCATION: (39)..(39)
<223> OTHER INFORMATION: An unnatural amino acid derivative analogous to
      the naturally occurring cysteine but with an extra
      methyl group in the side-chain

<400> SEQUENCE: 43

Val Glu Asn Lys Xaa Asn Lys Xaa Met Arg Asn Ala Tyr Trp Xaa Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Xaa
        35

<210> SEQ ID NO 44

```
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (9)..(11)
<223> OTHER INFORMATION: Any amino acid
<220> FEATURE:
<221> NAME/KEY: MOD_RES
<222> LOCATION: (13)..(14)
<223> OTHER INFORMATION: Any amino acid
<220> FEATURE:
<221> NAME/KEY: MOD_RES
<222> LOCATION: (17)..(18)
<223> OTHER INFORMATION: Any amino acid
<220> FEATURE:
<221> NAME/KEY: MOD_RES
<222> LOCATION: (24)..(25)
<223> OTHER INFORMATION: Any amino acid
<220> FEATURE:
<221> NAME/KEY: MOD_RES
<222> LOCATION: (27)..(28)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (35)..(35)
<223> OTHER INFORMATION: Any amino acid
<220> FEATURE:
<223> OTHER INFORMATION: see specification as filed for detailed
      description of substitutions and preferred embodiments

<400> SEQUENCE: 44

Val Xaa Asn Lys Phe Asn Lys Glu Xaa Xaa Xaa Ala Xaa Xaa Glu Ile
1               5                   10                  15

Xaa Xaa Leu Pro Asn Leu Asn Xaa Xaa Gln Xaa Xaa Ala Phe Ile Xaa
            20                  25                  30

Ser Leu Xaa Asp Asp Pro Ser
        35
```